(12) United States Patent
Manohar et al.

(10) Patent No.: US 12,195,811 B2
(45) Date of Patent: Jan. 14, 2025

(54) COMPOSITIONS AND METHODS FOR DETECTING SEVERE ACUTE RESPIRATORY SYNDROME CORONAVIRUS 2 (SARS-COV-2), INFLUENZA A AND INFLUENZA B

(71) Applicant: Roche Molecular Systems, Inc., Pleasanton, CA (US)

(72) Inventors: Chitra Manohar, San Ramon, CA (US); Marcel R. Fontecha, San Ramon, CA (US); Marintha Heil, Danville, CA (US); Ramani Sadanandam Ravirala, Dublin, CA (US); Christopher David Santini, Pleasant Hill, CA (US); Eugene Spier, Los Altos, CA (US); Jingtao Sun, San Ramon, CA (US); Thanh Tam, San Jose, CA (US); Huan Truong, Milpitas, CA (US); Michelle Elizabeth Yee, San Jose, CA (US); Kalyani Mangipudi, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 17/249,645

(22) Filed: Mar. 8, 2021

(65) Prior Publication Data

US 2021/0285061 A1 Sep. 16, 2021

Related U.S. Application Data

(60) Provisional application No. 63/122,869, filed on Dec. 8, 2020, provisional application No. 63/075,579, filed (Continued)

(51) Int. Cl.
*C12Q 1/68* (2018.01)
*C12Q 1/6818* (2018.01)
(Continued)

(52) U.S. Cl.
CPC ......... *C12Q 1/6888* (2013.01); *C12Q 1/6818* (2013.01); *C12Q 1/686* (2013.01); *C12Q 1/701* (2013.01)

(58) Field of Classification Search
CPC ....................................................... C12Q 1/68
(Continued)

(56) References Cited

U.S. PATENT DOCUMENTS

| 7,339,051 B2 | 3/2008 | Crooke et al. |
| 7,736,850 B2 | 6/2010 | Van Der Werf et al. |

(Continued)

FOREIGN PATENT DOCUMENTS

| WO | WO-2021263101 A1 * | 12/2021 | ............. C12Q 1/701 |
| WO | WO-2022050141 A1 * | 3/2022 | |

OTHER PUBLICATIONS

NCBI Accession No. MT276598 (Apr. 6, 2020).*

(Continued)

*Primary Examiner* — Aaron A Priest
(74) *Attorney, Agent, or Firm* — Daniel A. Blasiole; Daniel E. Agnew; David J. Chang

(57) ABSTRACT

Methods for the rapid detection of the presence or absence of SARS-CoV-2, influenza A and influenza B in a biological or non-biological sample are described. The methods can include performing an amplifying step, a hybridizing step, and a detecting step. Furthermore, primers and probes targeting SARS-CoV-2, influenza A, and influenza B and (Continued)

kits are provided that are designed for the detection of SARS-CoV-2, influenza A and influenza B.

12 Claims, 13 Drawing Sheets

Specification includes a Sequence Listing.

Related U.S. Application Data on Sep. 8, 2020, provisional application No. 62/987,066, filed on Mar. 9, 2020.

(51) Int. Cl.
| | | |
|---|---|---|
| *C12Q 1/686* | (2018.01) | |
| *C12Q 1/6888* | (2018.01) | |
| *C12Q 1/70* | (2006.01) | |

(58) Field of Classification Search
USPC .......................................................... 435/6.12
See application file for complete search history.

(56) References Cited

U.S. PATENT DOCUMENTS

| | | | |
|---|---|---|---|
| 2007/0042350 A1 | 2/2007 | Li et al. | |
| 2021/0285061 A1* | 9/2021 | Manohar | C12Q 1/6818 |
| 2021/0293815 A1* | 9/2021 | Rothberg | G01N 33/56983 |
| 2021/0327055 A1* | 10/2021 | Putha | G16H 50/80 |
| 2022/0017979 A1* | 1/2022 | Chu | C12Q 1/686 |
| 2022/0364157 A1* | 11/2022 | Hogan | C12Q 1/6876 |

OTHER PUBLICATIONS

Wu et al., Structure genomics of SARS-CoV-2 and its Omicron variant: drug design templates for COVID-19, Acta Pharmacol Sin. Dec. 2022;43(12):3021-3033. doi: 10.1038/s41401-021-00851-w. Epub Jan. 20, 2022.*
Shatavia Morrison, The SARS-CoV-2 genome, COVID-19 Genomic Epidemiology Toolkit: Module 1.2, available at https://www.cdc.gov/amd/pdf/slidesets/toolkitmodule_1.2-508c.pdf, accessed Apr. 2, 2024.*
Wikipedia, SARS-related coronavirus, available at https://en.wikipedia.org/wiki/SARS-related_coronavirus, accessed Apr. 1, 2024.*
How to design primers and probes for PCR and qPCR, available at https://www.idtdna.com/pages/education/decoded/article/designing-pcr-primers-and-probes, published Oct. 21, 2013.*
Lu, R. et al., "Genomic characterisation and epidemiology of 2019 novel coronavirus: implications for virus origins and receptor binding", the Lancet, Feb. 22, 2020, vol. 395, Issue 10224, pp. 565-574.
Wu, F. et al., "A new coronavirus associated with human respiratory disease in China", Nature, Mar. 12, 2020, vol. 579, pp. 265-269.
Corman, V.M. et al., "Detection of 2019 novel coronavirus (2019-nCoV) by real-time RT-PCR", Euro Surveill, Jan. 23, 2020, vol. 25(3), pp. 1-8.
Anonymous: "Detection of 2019 novel coronavirus (2019-nCOV) in suspected human cases by RT-PCR", i Jan. 2020 (Jan. 1, 2020), XP055830598, Retrieved from the Internet: URL: https://www.who.int/docs/default-source/coronaviruse/peiris-protocol-16-1-20.pdf ? sfvrsn=af 1aac73_4. [retrieved on Aug. 6, 2021].
Chu, D.K.W., et al., Molecular Diagnosis of a Novel Coronavirus (2019-nCoV) Causing an Outbreak of Pneumonia, Clinical Chemistry, Jan. 31, 2020, pp. 549-555, vol. 66, No. 4.
International Search Report issued Aug. 18, 2021 in Application No. PCT/EP2021/055748, 25 pages.
Mancini, F., et al., Multiplex Real-Time Reverse-Transcription Polymerase Chain Reaction Assays for Diagnostic Testing of Severe Acute Respiratory Syndrome Coronavirus 2 and Seasonal Influenza Viruses: A Challenge of the Phase 3 Pandemic Setting, The Journal of Infectious Diseases, Oct. 20, 2020, pp. 765-774, vol. 223, No. 5.
Pang, J., et al., Potential Rapid Diagnostics, Vaccine and Therapeutics for 2019 Novel Coronavirus (2019-nCOV): A Systematic Review, Journal of Clinical Medicine, Feb. 26, 2020, p. 623 (1-33), vol. 9, No. 3.
Partial International Search Report issued Jun. 2, 2021 in Application No. PCT/EP2021/055748, 18 pages.
Roche: "cobasR SARS-CoV-2", Mar. 1, 2020, XP055709557, Retrieved from the Internet: URL:https://www.who.int/diagnostics_laboratory/eul_0504-046-00_cobas_sars_cov2_qualitative_assay_ifu.pdf?ua=1.
WHO Team: "Molecular assays to diagnose COVID-19: Summary table of available protocols", Mar. 15, 2020, XP055732018, Retrieved from the Internet: https://www.who.int/docs/default-source/coronaviruse/whoinhouseassays.pdf?sfvrsn=de3a76aa_2&download=true.
Yu, X.-F., et al., Preparation of Armored RNA as a Control for Multiplex Real-Time Reverse Transcription-PCR Detection of Influenza Virus and Severe Acute Respiratory Syndrome Coronavirus, Journal of Clinical Microbiology, Dec. 26, 2007, pp. 837-841, vol. 46, No. 3.

* cited by examiner

| Levels: (RNA) | nCoV1 (Target 1) | Pan-Sarbecovirus 1 (Target 2) |
|---|---|---|
| Copies/PCR | Replicates Detected | Replicates Detected |
| 1.00E+08 | 10/10 | 10/10 |
| 1.00E+07 | 10/10 | 10/10 |
| 1.00E+06 | 10/10 | 10/10 |
| 1.00E+05 | 10/10 | 10/10 |
| 1.00E+04 | 10/10 | 10/10 |
| 1.00E+03 | 10/10 | 10/10 |
| 1.00E+02 | 10/10 | 10/10 |
| 1.00E+01 | 10/10 | 10/10 |

FIG. 6

SEQUENCE LISTING

```
<160> NUMBER OF SEQ ID NOS: 45

<210> SEQ ID NO 1
<211> LENGTH: 23
<212> TYPE: DNA
<213> ORGANISM: Artificial Sequence
<220> FEATURE:
<223> OTHER INFORMATION: Forward primer NCOV-1F.A
<220> FEATURE:
<221> NAME/KEY: modified_base
<222> LOCATION: (23)..(23)
<223> OTHER INFORMATION: t-butylbenzyl dA

<400> SEQUENCE: 1
tgattgttac gatggtggct gta                                           23

<210> SEQ ID NO 2
<211> LENGTH: 25
<212> TYPE: DNA
<213> ORGANISM: Artificial Sequence
<220> FEATURE:
<223> OTHER INFORMATION: Forward primer NCOV-2F
<220> FEATURE:
<221> NAME/KEY: modified_base
<222> LOCATION: (25)..(25)
<223> OTHER INFORMATION: t-butylbenzyl dA

<400> SEQUENCE: 2
ttcatccgga gttgttaatc cagta                                         25

<210> SEQ ID NO 3
<211> LENGTH: 20
<212> TYPE: DNA
<213> ORGANISM: Artificial Sequence
<220> FEATURE:
```

```
<223> OTHER INFORMATION: Forward primer NCOV-3F.A
<220> FEATURE:
<221> NAME/KEY: modified_base
<222> LOCATION: (20)..(20)
<223> OTHER INFORMATION: t-butylbenzyl dA

<400> SEQUENCE: 3
cccatgcttc agtcagctga                                          20

<210> SEQ ID NO 4
<211> LENGTH: 25
<212> TYPE: DNA
<213> ORGANISM: Artificial Sequence
<220> FEATURE:
<223> OTHER INFORMATION: Forward primer SARBV-1F.A
<220> FEATURE:
<221> NAME/KEY: modified_base
<222> LOCATION: (25)..(25)
<223> OTHER INFORMATION: t-butylbenzyl dA

<400> SEQUENCE: 4
tcttgctttc gtggtattct tgcta                                    25

<210> SEQ ID NO 5
<211> LENGTH: 27
<212> TYPE: DNA
<213> ORGANISM: Artificial Sequence
<220> FEATURE:
<223> OTHER INFORMATION: Forward primer SARBV-1F2.A
<220> FEATURE:
<221> NAME/KEY: modified_base
<222> LOCATION: (27)..(27)
<223> OTHER INFORMATION: t-butylbenzyl dA

<400> SEQUENCE: 5
gaacttatgt actcattcgt ttcggaa                                  27

<210> SEQ ID NO 6
<211> LENGTH: 19
<212> TYPE: DNA
<213> ORGANISM: Artificial Sequence
<220> FEATURE:
<223> OTHER INFORMATION: Forward primer SARBV-2F.A
<220> FEATURE:
<221> NAME/KEY: modified_base
<222> LOCATION: (19)..(19)
<223> OTHER INFORMATION: t-butylbenzyl dA

<400> SEQUENCE: 6
ccgtctgcgg aatgtggaa                                           19

<210> SEQ ID NO 7
<211> LENGTH: 25
<212> TYPE: DNA
<213> ORGANISM: Artificial Sequence
<220> FEATURE:
<223> OTHER INFORMATION: Reverse primer NCOV-1R.A
<220> FEATURE:
<221> NAME/KEY: modified_base
<222> LOCATION: (25)..(25)
<223> OTHER INFORMATION: t-butylbenzyl dA

<400> SEQUENCE: 7
agtgcatctt gatcctcata actca                                    25

<210> SEQ ID NO 8
<211> LENGTH: 30
<212> TYPE: DNA
<213> ORGANISM: Artificial Sequence
```

```
<220> FEATURE:
<223> OTHER INFORMATION: Reverse primer NCOV-1R1.A
<220> FEATURE:
<221> NAME/KEY: modified_base
<222> LOCATION: (30)..(30)
<223> OTHER INFORMATION: t-butylbenzyl dA

<400> SEQUENCE: 8
gcatcttgat cctcataact cattgaatca                                    30

<210> SEQ ID NO 9
<211> LENGTH: 31
<212> TYPE: DNA
<213> ORGANISM: Artificial Sequence
<220> FEATURE:
<223> OTHER INFORMATION: Reverse primer NCOV-1R2.A
<220> FEATURE:
<221> NAME/KEY: modified_base
<222> LOCATION: (31)..(31)
<223> OTHER INFORMATION: t-butylbenzyl dA

<400> SEQUENCE: 9
actcattgaa tcataataaa gtctagcctt a                                  31

<210> SEQ ID NO 10
<211> LENGTH: 27
<212> TYPE: DNA
<213> ORGANISM: Artificial Sequence
<220> FEATURE:
<223> OTHER INFORMATION: Reverse primer NCOV-2R
<220> FEATURE:
<221> NAME/KEY: modified_base
<222> LOCATION: (27)..(27)
<223> OTHER INFORMATION: t-butylbenzyl dA

<400> SEQUENCE: 10
acgaatgagt acataagttc gtactca                                       27

<210> SEQ ID NO 11
<211> LENGTH: 24
<212> TYPE: DNA
<213> ORGANISM: Artificial Sequence
<220> FEATURE:
<223> OTHER INFORMATION: Reverse primer NCOV-2R1.A
<220> FEATURE:
<221> NAME/KEY: modified_base
<222> LOCATION: (24)..(24)
<223> OTHER INFORMATION: t-butylbenzyl dA

<400> SEQUENCE: 11
tctcttccga aacgaatgag taca                                          24

<210> SEQ ID NO 12
<211> LENGTH: 23
<212> TYPE: DNA
<213> ORGANISM: Artificial Sequence
<220> FEATURE:
<223> OTHER INFORMATION: Reverse primer NCOV-2R2.A
<220> FEATURE:
<221> NAME/KEY: modified_base
<222> LOCATION: (23)..(23)
<223> OTHER INFORMATION: t-butylbenzyl dA

<400> SEQUENCE: 12
cctgtctctt ccgaaacgaa tga                                           23

<210> SEQ ID NO 13
<211> LENGTH: 28
<212> TYPE: DNA
```

<213> ORGANISM: Artificial Sequence
<220> FEATURE:
<223> OTHER INFORMATION: Reverse primer NCOV-3R1.A
<220> FEATURE:
<221> NAME/KEY: modified_base
<222> LOCATION: (28)..(28)
<223> OTHER INFORMATION: t-butylbenzyl dA

<400> SEQUENCE: 13
gcaaaaccag ctactttatc attgtaga                28

<210> SEQ ID NO 14
<211> LENGTH: 28
<212> TYPE: DNA
<213> ORGANISM: Artificial Sequence
<220> FEATURE:
<223> OTHER INFORMATION: Reverse primer NCOV-3R2.A
<220> FEATURE:
<221> NAME/KEY: modified_base
<222> LOCATION: (28)..(28)
<223> OTHER INFORMATION: t-butylbenzyl dA

<400> SEQUENCE: 14
tcattgtaga tgtcaaaagc cctgtata                28

<210> SEQ ID NO 15
<211> LENGTH: 26
<212> TYPE: DNA
<213> ORGANISM: Artificial Sequence
<220> FEATURE:
<223> OTHER INFORMATION: Reverse primer SARBV-1R.A
<220> FEATURE:
<221> NAME/KEY: modified_base
<222> LOCATION: (26)..(26)
<223> OTHER INFORMATION: t-butylbenzyl dA

<400> SEQUENCE: 15
ctcacgttaa caatattgca gcagta                26

<210> SEQ ID NO 16
<211> LENGTH: 25
<212> TYPE: DNA
<213> ORGANISM: Artificial Sequence
<220> FEATURE:
<223> OTHER INFORMATION: Reverse primer SARBV-1R1.A
<220> FEATURE:
<221> NAME/KEY: modified_base
<222> LOCATION: (25)..(25)
<223> OTHER INFORMATION: t-butylbenzyl dA

<400> SEQUENCE: 16
aactcacgtt aacaatattg cagca                25

<210> SEQ ID NO 17
<211> LENGTH: 30
<212> TYPE: DNA
<213> ORGANISM: Artificial Sequence
<220> FEATURE:
<223> OTHER INFORMATION: Reverse primer SARBV-1R2.A
<220> FEATURE:
<221> NAME/KEY: modified_base
<222> LOCATION: (30)..(30)
<223> OTHER INFORMATION: t-butylbenzyl dA

<400> SEQUENCE: 17
ttttactaga ctcacgttaa caatattgca                30

<210> SEQ ID NO 18
<211> LENGTH: 22

<212> TYPE: DNA
<213> ORGANISM: Artificial Sequence
<220> FEATURE:
<223> OTHER INFORMATION: Reverse primer SARBV-2R.A
<220> FEATURE:
<221> NAME/KEY: modified_base
<222> LOCATION: (22)..(22)
<223> OTHER INFORMATION: t-butylbenzyl dA

<400> SEQUENCE: 18
acttacaccg caaacccgtt ta                                    22

<210> SEQ ID NO 19
<211> LENGTH: 18
<212> TYPE: DNA
<213> ORGANISM: Artificial Sequence
<220> FEATURE:
<223> OTHER INFORMATION: Reverse primer SARBV-2R1.A
<220> FEATURE:
<221> NAME/KEY: modified_base
<222> LOCATION: (18)..(18)
<223> OTHER INFORMATION: t-butylbenzyl dA

<400> SEQUENCE: 19
gtgccgcacg gtgtaaga                                         18

<210> SEQ ID NO 20
<211> LENGTH: 21
<212> TYPE: DNA
<213> ORGANISM: Artificial Sequence
<220> FEATURE:
<223> OTHER INFORMATION: Reverse primer SARBV-2R2.A
<220> FEATURE:
<221> NAME/KEY: modified_base
<222> LOCATION: (21)..(21)
<223> OTHER INFORMATION: t-butylbenzyl dA

<400> SEQUENCE: 20
gtgtaagacg ggctgcactt a                                     21

<210> SEQ ID NO 21
<211> LENGTH: 36
<212> TYPE: DNA
<213> ORGANISM: Artificial Sequence
<220> FEATURE:
<223> OTHER INFORMATION: Probe WUHAN-4P
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (6)..(7)
<223> OTHER INFORMATION: BHQ-2 Quencher

<400> SEQUENCE: 21
tcatcgtcaa caacctagac aaatcagctg gttttc                     36

<210> SEQ ID NO 22
<211> LENGTH: 31
<212> TYPE: DNA
<213> ORGANISM: Artificial Sequence
<220> FEATURE:
<223> OTHER INFORMATION: Probe NCOV-2P
<220> FEATURE:
<221> NAME/KEY: misc_feature
<223> OTHER INFORMATION: 5' FAM
<220> FEATURE:
<221> NAME/KEY: misc_feature

```
<223> OTHER INFORMATION: 3' Spacer-C3 Blocker
<220> FEATURE:
<221> NAME/KEY: misc_feature
<222> LOCATION: (8)..(9)
<223> OTHER INFORMATION: BHQ-2 Quencher

<400> SEQUENCE: 22
cgacgacgac tactagcgtg cctttgtaag c                              31

<210> SEQ ID NO 23
<211> LENGTH: 30
<212> TYPE: DNA
<213> ORGANISM: Artificial Sequence
<220> FEATURE:
<223> OTHER INFORMATION: Probe NCOV-3P8Q
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (8)..(9)
<223> OTHER INFORMATION: BHQ-2 Quencher

<400> SEQUENCE: 23
cgtgcggcac aggcactagt actgatgtcg                                30

<210> SEQ ID NO 24
<211> LENGTH: 30
<212> TYPE: DNA
<213> ORGANISM: Artificial Sequence
<220> FEATURE:
<223> OTHER INFORMATION: Probe SARBV-P1
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (8)..(9)
<223> OTHER INFORMATION: BHQ-2 Quencher

<400> SEQUENCE: 24
agccatcctt actgcgcttc gattgtgtgc                                30

<210> SEQ ID NO 25
<211> LENGTH: 30
<212> TYPE: DNA
<213> ORGANISM: Artificial Sequence
<220> FEATURE:
<223> OTHER INFORMATION: Probe SARBV-P1_6Q.P
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' Phosphate
<220> FEATURE:
<221> NAME/KEY: misc_feature
<222> LOCATION: (6)..(7)
<223> OTHER INFORMATION: BHQ-2 Quencher

<400> SEQUENCE: 25
agccatcctt actgcgcttc gattgtgtgc                                30

<210> SEQ ID NO 26
<211> LENGTH: 30
```

```
<212> TYPE: DNA
<213> ORGANISM: Artificial Sequence
<220> FEATURE:
<223> OTHER INFORMATION: Probe SARBV-P2
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (7)..(8)
<223> OTHER INFORMATION: BHQ-2 Quencher

<400> SEQUENCE: 26
atggctgtag ttgtgaccaa ctccgcgaac                                          30

<210> SEQ ID NO 27
<211> LENGTH: 30
<212> TYPE: DNA
<213> ORGANISM: Artificial Sequence
<220> FEATURE:
<223> OTHER INFORMATION: Forward primer NCOV-1-FN1.A
<220> FEATURE:
<221> NAME/KEY: modified_base
<222> LOCATION: (30)..(30)
<223> OTHER INFORMATION: t-butylbenzyl dA

<400> SEQUENCE: 27
ctttgattgt tacgatggtg gctgtattaa                                          30

<210> SEQ ID NO 28
<211> LENGTH: 28
<212> TYPE: DNA
<213> ORGANISM: Artificial Sequence
<220> FEATURE:
<223> OTHER INFORMATION: Forward primer NCOV-1-FN3.A
<220> FEATURE:
<221> NAME/KEY: modified_base
<222> LOCATION: (28)..(28)
<223> OTHER INFORMATION: t-butylbenzyl dA

<400> SEQUENCE: 28
tactttgatt gttacgatgg tggctgta                                            28

<210> SEQ ID NO 29
<211> LENGTH: 31
<212> TYPE: DNA
<213> ORGANISM: Artificial Sequence
<220> FEATURE:
<223> OTHER INFORMATION: Forward primer NCOV-2-FN2.A
<220> FEATURE:
<221> NAME/KEY: modified_base
<222> LOCATION: (31)..(31)
<223> OTHER INFORMATION: t-butylbenzyl dA

<400> SEQUENCE: 29
tactttgatt gttacgatgg tggctgtatt a                                        31

<210> SEQ ID NO 30
<211> LENGTH: 29
<212> TYPE: DNA
<213> ORGANISM: Artificial Sequence
<220> FEATURE:
<223> OTHER INFORMATION: Forward primer NCOV-4-FN4.A
<220> FEATURE:
<221> NAME/KEY: modified_base
<222> LOCATION: (29)..(29)
<223> OTHER INFORMATION: t-butylbenzyl dA
```

```
<400> SEQUENCE: 30
ttgttacgat ggtggctgta ttaatgcta                                    29

<210> SEQ ID NO 31
<211> LENGTH: 27
<212> TYPE: DNA
<213> ORGANISM: Artificial Sequence
<220> FEATURE:
<223> OTHER INFORMATION: Forward primer NCOV-4-FN5.A
<220> FEATURE:
<221> NAME/KEY: modified_base
<222> LOCATION: (27)..(27)
<223> OTHER INFORMATION: t-butylbenzyl dA

<400> SEQUENCE: 31
gatggtggct gtattaatgc taaccaa                                      27

<210> SEQ ID NO 32
<211> LENGTH: 29
<212> TYPE: DNA
<213> ORGANISM: Artificial Sequence
<220> FEATURE:
<223> OTHER INFORMATION: Probe SARBV-P1-N2_6Q.C3
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (7)..(8)
<223> OTHER INFORMATION: BHQ-2 Quencher

<400> SEQUENCE: 32
atccttactg cgcttcgatt gtgtgcgta                                    29

<210> SEQ ID NO 33
<211> LENGTH: 25
<212> TYPE: DNA
<213> ORGANISM: Artificial Sequence
<220> FEATURE:
<223> OTHER INFORMATION: Forward primer FLUAF M1 121 146
<220> FEATURE:
<221> NAME/KEY: modified_base
<222> LOCATION: (25)..(25)
<223> OTHER INFORMATION: t-butylbenzyl dA

<400> SEQUENCE: 33
gctctcatgg aatggctaaa gacaa                                        25

<210> SEQ ID NO 34
<211> LENGTH: 18
<212> TYPE: DNA
<213> ORGANISM: Artificial Sequence
<220> FEATURE:
<223> OTHER INFORMATION: Reverse primer FLUA_RP4_A
<220> FEATURE:
<221> NAME/KEY: modified_base
<222> LOCATION: (18)..(18)
<223> OTHER INFORMATION: t-butylbenzyl dC

<400> SEQUENCE: 34
tggacaaagc gtctacgc                                                18

<210> SEQ ID NO 35
<211> LENGTH: 31
<212> TYPE: DNA
<213> ORGANISM: Artificial Sequence
```

```
<220> FEATURE:
<223> OTHER INFORMATION: Probe FLUAP.H.C3_M1_212_181.6COU1.C
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (6)..(7)
<223> OTHER INFORMATION: BHQ-2 Quencher

<400> SEQUENCE: 35
cactgggcac ggtgagcgtg aacacaaatc c                              31

<210> SEQ ID NO 36
<211> LENGTH: 22
<212> TYPE: DNA
<213> ORGANISM: Artificial Sequence
<220> FEATURE:
<223> OTHER INFORMATION: Forward primer FLUBF NS1.749 770
<220> FEATURE:
<221> NAME/KEY: modified_base
<222> LOCATION: (22)..(22)
<223> OTHER INFORMATION: t-butylbenzyl dA

<400> SEQUENCE: 36
aagatggcca tcggatcctc aa                                        22

<210> SEQ ID NO 37
<211> LENGTH: 24
<212> TYPE: DNA
<213> ORGANISM: Artificial Sequence
<220> FEATURE:
<223> OTHER INFORMATION: Reverse primer FLUBR_NS1.865_842
<220> FEATURE:
<221> NAME/KEY: modified_base
<222> LOCATION: (24)..(24)
<223> OTHER INFORMATION: t-butylbenzyl dA

<400> SEQUENCE: 37
ggtgctcttg accaaattgg gata                                      24

<210> SEQ ID NO 38
<211> LENGTH: 32
<212> TYPE: DNA
<213> ORGANISM: Artificial Sequence
<220> FEATURE:
<223> OTHER INFORMATION: Probe FLUB_PRB2_11Q_JA270.C3
<220> FEATURE:
<221> NAME/KEY: misc_feature
<223> OTHER INFORMATION: 5' JA270-Thr
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (11)..(12)
<223> OTHER INFORMATION: BHQ-2 Quencher

<400> SEQUENCE: 38
cattcaaagc caattcgagc agctgaaact gc                             32

<210> SEQ ID NO 39
<211> LENGTH: 20
<212> TYPE: DNA
<213> ORGANISM: Artificial Sequence
<220> FEATURE:
<223> OTHER INFORMATION: Forward primer NCOV-F.core
```

<400> SEQUENCE: 39
ttgttacgat ggtggctgta                                          20

<210> SEQ ID NO 40
<211> LENGTH: 31
<212> TYPE: DNA
<213> ORGANISM: Artificial Sequence
<220> FEATURE:
<223> OTHER INFORMATION: Forward primer NCOV-N3-F3.A
<220> FEATURE:
<221> NAME/KEY: modified_base
<222> LOCATION: (31)..(31)
<223> OTHER INFORMATION: t-butylbenzyl dC

<400> SEQUENCE: 40
ttttacactt aaaaacacag tctgtaccgt c                             31

<210> SEQ ID NO 41
<211> LENGTH: 27
<212> TYPE: DNA
<213> ORGANISM: Artificial Sequence
<220> FEATURE:
<223> OTHER INFORMATION: Reverse primer NCOV-N3-R1.A
<220> FEATURE:
<221> NAME/KEY: modified_base
<222> LOCATION: (27)..(27)
<223> OTHER INFORMATION: t-butylbenzyl dA

<400> SEQUENCE: 41
aacccgttta aaaacgattg tgcatca                                  27

<210> SEQ ID NO 42
<211> LENGTH: 36
<212> TYPE: DNA
<213> ORGANISM: Artificial Sequence
<220> FEATURE:
<223> OTHER INFORMATION: Probe NCOV-4P-JA270-Q10.P
<220> FEATURE:
<221> NAME/KEY: misc_feature
<223> OTHER INFORMATION: 5' JA270-Thr
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (10)..(11)
<223> OTHER INFORMATION: BHQ-2 Quencher

<400> SEQUENCE: 42
tcatcgtcaa caacctagac aaatcagctg gttttc                        36

<210> SEQ ID NO 43
<211> LENGTH: 29
<212> TYPE: DNA
<213> ORGANISM: Artificial Sequence
<220> FEATURE:
<223> OTHER INFORMATION: Probe NCOV-N3-JA
<220> FEATURE:
<221> NAME/KEY: misc_feature
<223> OTHER INFORMATION: 5' JA270-Thr
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (12)..(13)
<223> OTHER INFORMATION: BHQ-2 Quencher

<400> SEQUENCE: 43
tccgcgaacc catgcttcag tcagctgat                                29

```
<210> SEQ ID NO 44
<211> LENGTH: 31
<212> TYPE: DNA
<213> ORGANISM: Artificial Sequence
<220> FEATURE:
<223> OTHER INFORMATION: Probe FLUAP.H.C3_M1_212_181.6
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (6)..(7)
<223> OTHER INFORMATION: BHQ-2 Quencher

<400> SEQUENCE: 44
cactgggcac ggtgagcgtg aacacaaatc c                              31

<210> SEQ ID NO 45
<211> LENGTH: 32
<212> TYPE: DNA
<213> ORGANISM: Artificial Sequence
<220> FEATURE:
<223> OTHER INFORMATION: Probe FLUB_THRBP2_K77
<220> FEATURE:
<221> NAME/KEY: misc_feature
<223> OTHER INFORMATION: 5' BHQ-2 Quencher
<220> FEATURE:
<221> NAME/KEY: misc_feature
<223> OTHER INFORMATION: 3' Spacer-C3 Blocker
<220> FEATURE:
<221> NAME/KEY: misc_feature
<222> LOCATION: (2)..(2)
<223> OTHER INFORMATION: D-Locked Nucleic Acid
<220> FEATURE:
<221> NAME/KEY: misc_feature
<222> LOCATION: (9)..(10)
<223> OTHER INFORMATION: DBCO-Thr

<400> SEQUENCE: 45
cattcaaagc caattcgagc agctgaaact gc                             32
```

COMPOSITIONS AND METHODS FOR DETECTING SEVERE ACUTE RESPIRATORY SYNDROME CORONAVIRUS 2 (SARS-COV-2), INFLUENZA A AND INFLUENZA B

CROSS REFERENCE TO RELATED APPLICATIONS

This application claims the benefit of priority to U.S. Provisional Application No. 62/987,066, filed on Mar. 9, 2020, U.S. Provisional Application No. 63/075,579, filed on Sep. 8, 2020, and U.S. Provisional Application No. 63/122,869, filed on Dec. 8, 2020, each of which is hereby incorporated in its entirety by reference.

REFERENCE TO SEQUENCE LISTING

This application contains a Sequence Listing submitted as an electronic text file named "35962_US3_ST25.txt", having a size in bytes of 14 kb, and created on Jan. 25, 2021.

FIELD OF THE INVENTION

The present disclosure relates to the field of viral diagnostics, and more particularly to detection of Severe Acute Respiratory Syndrome Coronavirus 2 (SARS-CoV-2) or of SARS-CoV-2, Influenza A Virus (Influenza A) and Influenza B Virus (Influenza B).

BACKGROUND OF THE INVENTION

Viruses of the family Coronaviridae possess a single stranded, positive-sense RNA genome ranging from 26 to 32 kilobases in length. Coronaviruses have been identified in several avian hosts, as well as in various mammals, including camels, bats, masked palm civets, mice, dogs, and cats. Novel mammalian coronaviruses are now regularly identified. For example, an HKU2-related coronavirus of bat origin was responsible for a fatal acute diarrhoea syndrome in pigs in 2018.

Among the several coronaviruses that are pathogenic to humans, most are associated with mild clinical symptoms, with two notable exceptions: severe acute respiratory syndrome (SARS) coronavirus (SARS-CoV), a novel betacoronavirus that emerged in Guangdong, southern China, in November, 2002, and resulted in more than 8000 human infections and 774 deaths in 37 countries during 2002-03; and Middle East respiratory syndrome (MERS) coronavirus (MERS-CoV), which was first detected in Saudi Arabia in 2012 and was responsible for 2494 laboratory-confirmed cases of infection and 858 fatalities since September, 2012, including 38 deaths following a single introduction into South Korea.

In late December, 2019, several patients with viral pneumonia were found to be epidemiologically associated with a market in Wuhan, in the Hubei province of China, where a number of non-aquatic animals such as birds and rabbits were also on sale before the outbreak. A novel, human-infecting coronavirus, initially named 2019 novel coronavirus (2019-nCoV), was identified with use of next-generation sequencing. This novel coronavirus is classified under the family Coronavirus, genus Betacoronavirus and subgenus Sarbecovirus and is described in "Genomic characterization and epidemiology of 2019 novel coronavirus: implications for virus origins and receptor binding" by Lu, R. et al., Lancet, 2020, Vol. 395, p. 565-574, hereby incorporated by reference in its entirety. The International Committee on Taxonomy of Viruses (ICTV) announced the formal name for the virus as Severe Acute Respiratory Syndrome Coronavirus 2 (SARS-CoV-2). As of Mar. 1, 2020, almost 80,000 confirmed cases and over 2800 fatalities have been reported in China, and SARS-CoV-2 has been detected in at least 60 locations internationally, including in the United States. Thus, there is a need in the art for a quick, reliable, specific, and sensitive method to detect SARS-CoV-2.

Influenza, or flu, is a highly contagious viral respiratory disease of the family Orthomyxoviridae. Flu infections can occur anytime, but are usually characterized by seasonal outbreaks during the winter months in each hemisphere. Symptoms vary widely in severity from patient to patient, but typically include one or more of cough, fever, runny or stuffy nose, sore throat, body aches, and fatigue. While flu can infect anyone, it is especially dangerous to the elderly and the very young, as well as those with diminished immune capacity and certain pre-existing conditions.

There are four known types of influenza virus, denoted influenza virus A through D. Humans can be infected by influenza virus A, B, and C, but no cases of influenza D infections of humans have been reported. The most common type infecting humans is influenza A, followed by influenza B. Influenza A is further divided into serotypes based on variations in two proteins, hemaggluttinin (H) and neuraminidase (N), found on the outer surface of viral particles. Hemagglutinin variants H1-H3, and neuraminidase variants N1 and N2, form the most common serotypes that arise during seasonal outbreaks. In some years, influenza A outbreaks have had devastating worldwide impacts, resulting in flu pandemics. For example, the 1918 Spanish flu pandemic is estimated to have killed between 17 million and 50 million people. The Asian flu pandemic of 1957, and the Hong Kong flu pandemic of 1968, each killed a million or more people. The influenza A H1N1 serotype was responsible for the 1918 Spanish flu, while the H2N2 and H3N2 serotypes were the causative agents of the Asian flu and Hong Kong flu pandemics, respectively.

Influenza B and influenza C, while capable of infecting humans, are far less dangerous. Influenza B has a single serotype, and thus it is easier to establish and maintain population immunity against this virus. Nonetheless, significant infections of children and adolescents, and even localized epidemics, can occur with this virus. Influenza C, while capable of infecting humans, is even less dangerous than influenza B, and patients exhibit only mild symptoms.

Hence, beyond the need for a quick, reliable, specific, and sensitive method to detect SARS-CoV-2 as such, also rapid and accurate diagnosis and differentiation of SARS-CoV-2 and influenza infections is important in individuals suspected of a respiratory infection. The seasonality ranges of SARS-CoV-2 and influenza overlap and the clinical manifestations of the two diseases can be similar, ranging from asymptomatic or mild "influenza-like" illness (such as fever, cough, shortness of breath, or myalgia) in a majority of individuals to more severe and life-threatening disease. However, the two virus types differ in that SARS-CoV-2 patients can spread infection while presymptomatic, while influenza patients develop symptoms more quickly and do not shed virus while presymptomatic. As a result, rapid and accurate detection and differentiation of both SARS-CoV-2 and influenza can help to inform time-critical medical decision-making, facilitate infection control efforts, promote efficient resourcing, optimize use of targeted therapies and antimicrobials, and reduce ancillary testing or procedures. Thus, there is a need in the art for a quick, reliable, specific, and sensitive method to detect and differentiate SARS-CoV-2, influenza A, and influenza B.

SUMMARY OF THE INVENTION

The present disclosure provides methods for the rapid detection of the presence or absence of SARS-CoV-2 in a biological or non-biological sample, for example, multiplex detection of SARS-CoV-2 by qualitative or quantitative real-time reverse-transcription polymerase chain reaction (RT-PCR) in a single test tube or a single well. The present disclosure also provides methods for the rapid and simultaneous detection of the presence or absence of SARS-CoV-2, influenza A and influenza B in a biological or non-biological sample, for example, multiplex detection of SARS-CoV-2, influenza A and influenza B by qualitative or quantitative real-time reverse-transcription polymerase chain reaction (RT-PCR) in a single test tube or a single well. Embodiments include methods of detection of SARS-CoV-2, influenza A and influenza B comprising performing a reverse transcription step and at least one cycling step, which may include an amplifying step and a hybridizing step. Furthermore, embodiments include primers, probes, and kits that are designed for the detection of SARS-CoV-2 or for the multiplex detection of SARS-CoV-2, influenza A and influenza B in a single tube or a single well. The detection methods are designed to target various regions of each of the target genomes. For example, the methods are designed to target the region of the SARS-CoV-2 genome that encodes the structural envelope (E) region, and/or the non-structural Open Reading Frame (ORF1a/b gene coding for the ORF1a polyprotein and the ORF1a/b polyprotein) region. The methods may also be designed to target other regions of the SARS-CoV-2 genome, alone or in combination, such as S gene (coding for spike protein responsible for binding to cell receptor), ORF3ab, E gene (coding for envelope protein), and M gene (coding for membrane protein). In addition, there are 265 bases of non-coding region at the 5' terminal end and 229 bases of non-coding region at the 3' terminal end of the SARS-CoV-2 genome, and these may be targeted as well.

With respect to influenza A and B, the methods may be designed to target any gene or non-coding regions within the eight segments that make up their genomes. For example, for influenza A, the methods may be designed to target the influenza A Segment 7 matrix protein 2 (M2) and matrix protein 1 (M1) sequences. For influenza B, the methods may be designed to target the influenza B Segment 8 nuclear export protein (NEP) and nonstructural protein 1 (NS1) sequences.

The methods for the simultaneous detection of SARS-CoV-2, influenza A and influenza B by RT-PCR in a single test tube or single well may also include simultaneously detecting by RT-PCR in a single test tube or single well additional viruses that may cause respiratory disease in humans, especially in the upper respiratory tract. Examples of these viruses include but are not limited to: Coronavirus (229E, NL63, OC43, HKU1), Respiratory Syncytial Virus, Human Metapneumovirus, Adenovirus (B,E,U,C), Enterovirus, Rhinovirus, and Human Parainfluenza Virus (1, 2, 3, 4).

In one embodiment, a method for detecting SARS-CoV-2 in a sample is provided, comprising performing an amplifying step including contacting the sample with a set of primers to produce an amplification product if SARS-CoV-2 is present in the sample; performing a hybridizing step including contacting the amplification product with one or more detectable probes; and detecting the presence or absence of the amplified product, wherein the presence of the amplified product is indicative of the presence of SARS-CoV-2 in the sample and wherein the absence of the amplified product is indicative of the absence of SARS-CoV-2 in the sample; wherein the set of primer comprises or consists of an oligonucleotide sequence selected from the group consisting of SEQ ID NOs: 1-20, 27-31, and 40-41 or a complement thereof; and wherein the one or more detectable probes comprises or consists of an oligonucleotide sequence selected from the group consisting of SEQ ID NOs: 21-26, 32, and 42-43 or a complement thereof.

In one embodiment, a multiplex method for detecting SARS-CoV-2 in a sample is provided, comprising performing an amplifying step including contacting the sample with a first set of primers to produce an amplification product if SARS-CoV-2 is present in the sample and a second set of primers to produce an amplification product if SARS-CoV-2 is present in the sample; performing a hybridizing step including contacting the amplification products with at least one detectable probe hybridizing to an amplification product produced by the first primer pair and with at least one second detectable probe hybridizing to an amplification product produced by the second primer pair; and detecting the presence or absence of the amplified product(s), wherein the presence of the amplified product(s) is indicative of the presence of SARS-CoV-2 in the sample and wherein the absence of the amplified product is indicative of the absence of SARS-CoV-2 in the sample; wherein the first set of primers comprises or consists of a forward primer oligonucleotide sequence selected from the group consisting of SEQ ID NOs: 1-3, and 27-31, and a reverse primer oligonucleotide sequence selected from the group consisting of SEQ ID NOs: 7-14; and the second set of primers comprises or consists of a forward primer oligonucleotide sequence selected from the group consisting of SEQ ID NOs: 4-6, and 40 and a reverse primer oligonucleotide sequence selected from the group consisting of SEQ ID NOs: 15-20, and 41; and wherein the at least one detectable probe hybridizing to an amplification product produced by the first primer pair comprises or consists of an oligonucleotide sequence selected from the group consisting of SEQ ID NOs: 21-23, and 42, or a complement thereof and wherein the at least one detectable probe hybridizing to an amplification product produced by the second primer pair comprises or consists of an oligonucleotide sequence selected from the group consisting of SEQ ID NOs: 24-26, 32, and 43 or a complement thereof.

In some embodiments, the first primer pair specifically hybridizes to and amplifies the SARS-CoV-2 target nucleic acid and the second primer pair hybridizes to and amplifies the SARS-CoV-2 target nucleic acid. In some embodiments the second primer pair hybridizes to and amplifies the SARS-CoV-2 target nucleic acid and other coronavirus target nucleic acids from the subgenus Sarbecovirus. In some embodiments, the at least one detectable probe hybridizing to an amplification product produced by the first primer pair specifically hybridizes to the SARS-CoV-2 target nucleic acid. In some embodiments, the at least one detectable probe hybridizing to an amplification product produced by the second primer pair hybridizes to the SARS-CoV-2 target nucleic acid. In some embodiments, the at least one detectable probe hybridizing to an amplification product produced by the second primer pair hybridizes to the SARS-CoV-2 target nucleic acid and other coronavirus target nucleic acids from the subgenus Sarbecovirus.

In one embodiment, the set of primers for amplification of the SARS-CoV-2 target includes a first primer comprising or consisting a first oligonucleotide sequence selected from the group consisting of SEQ ID NOs: 1-6, 27-31, and 40 or a complement thereof, and a second primer comprising or consisting a second oligonucleotide sequence selected from the group consisting of SEQ ID NOs: 7-20, and 41, or a complement thereof, and the one or more detectable probes for detection of the amplification product comprises or consists of an oligonucleotide sequence selected from the group consisting of SEQ ID NOs: 21-26, 32, 42, and 43 or a complement thereof.

In one embodiment, the set of primers for specific amplification of the SARS-CoV-2 target includes a first primer comprising or consisting a first oligonucleotide sequence selected from the group consisting of SEQ ID NOs: 1-3, and 27-31, and a second primer comprising or consisting a second oligonucleotide sequence selected from the group consisting of SEQ ID NOs: 7-14, and the one or more detectable probes for detection of the amplification product comprises or consists of an oligonucleotide sequence selected from the group consisting of SEQ ID NOs: 21-23, and 42, or a complement thereof.

In one embodiment, the set of primers for specific amplification of the SARS-CoV-2 target includes a first primer comprising or consisting a first oligonucleotide sequence of SEQ ID NO: 40, and a second primer comprising or consisting a second oligonucleotide sequence of SEQ ID NO: 41, and the one or more detectable probes for detection of the amplification product comprises or consists of an oligonucleotide sequence of SEQ ID NO: 43, or a complement thereof.

In one embodiment, the set of primers for amplification of the SARS-CoV-2 target includes a first primer comprising or consisting a first oligonucleotide sequence selected from the group consisting of SEQ ID NOs: 4-6, and a second primer comprising or consisting a second oligonucleotide sequence selected from the group consisting of SEQ ID NOs: 15-20, and the one or more detectable probes for detection of the amplification product comprises or consists of an oligonucleotide sequence selected from the group consisting of SEQ ID NOs: 24-26 and 32, or a complement thereof. In some embodiments, the set of primers is suitable for amplification of SARS-CoV-2 target nucleic acid and other coronavirus target nucleic acids from the subgenus Sarbecovirus.

In another embodiment, the set of primers for amplification of the SARS-CoV-2 target includes a first primer comprising or consisting of an oligonucleotide sequence of SEQ ID NO: 1, and a second primer comprising or consisting of an oligonucleotide sequence of SEQ ID NO: 7, and a detectable probe that comprises or consists of an oligonucleotide sequence of SEQ ID NO: 21. In another embodiment, the first primer comprises or consists of an oligonucleotide sequence selected from the group consisting of SEQ ID NOs: 27 and 30, the second primer comprises or consists of an oligonucleotide sequence of SEQ ID NO: 7, and a detectable probe that comprises or consists of an oligonucleotide sequence of SEQ ID NO: 21. In another embodiment, the first primer comprises or consists of an oligonucleotide sequence of SEQ ID NO: 5, the second primer comprises or consists of an oligonucleotide sequence of SEQ ID NO: 15, and the detectable probe comprises or consists of an oligonucleotide sequence selected from the group consisting of SEQ ID NO: 25 and 32. In yet another embodiment, the first primer comprises or consists of an oligonucleotide sequence of SEQ ID NO: 6, the second primer comprises or consists of an oligonucleotide sequence of SEQ ID NO: 18, and the detectable probe comprises or consists of an oligonucleotide sequence of SEQ ID NO: 26.

In one embodiment, the set of primers for amplification of the SARS-CoV-2 target includes a first primer comprising or consisting a first oligonucleotide sequence selected from the group consisting of SEQ ID NOs: 1-6 and 27-31, and 40, and a second primer comprising or consisting a second oligonucleotide sequence selected from the group consisting of SEQ ID NOs: 7-20, and 41.

In one embodiment, the set of primers for amplification of the SARS-CoV-2 target includes a first primer comprising or consisting a first oligonucleotide sequence selected from the group consisting of SEQ ID NOs: 1-3 and 27-31, and a second primer comprising or consisting a second oligonucleotide sequence selected from the group consisting of SEQ ID NOs: 7-14. In another embodiment, the set of primers for amplification of the SARS-CoV-2 target includes a first primer comprising or consisting a first oligonucleotide sequence selected from the group consisting of SEQ ID NOs: 4-6, or a complement thereof, and a second primer comprising or consisting a second oligonucleotide sequence selected from the group consisting of SEQ ID NOs: 15-20, or a complement thereof. In another embodiment, the set of primers for amplification of the SARS-CoV-2 target includes a first primer comprising or consisting of an oligonucleotide sequence of SEQ ID NO: 1, and a second primer comprising or consisting of an oligonucleotide sequence of SEQ ID NO: 7. In another embodiment, the first primer comprises or consists of an oligonucleotide sequence selected from the group consisting of SEQ ID NOs: 27 and 30, the second primer comprises or consists of an oligonucleotide sequence of SEQ ID NO: 7. In another embodiment, the first primer comprises or consists of an oligonucleotide sequence of SEQ ID NO: 5, the second primer comprises or consists of an oligonucleotide sequence of SEQ ID NO: 15. In yet another embodiment, the first primer comprises or consists of an oligonucleotide sequence of SEQ ID NO: 6, the second primer comprises or consists of an oligonucleotide sequence of SEQ ID NO: 18. In yet another embodiment, the first primer comprises or consists of an oligonucleotide sequence of SEQ ID NO: 40, the second primer comprises or consists of an oligonucleotide sequence of SEQ ID NO: 41.

In another embodiment, the set of primers for amplification of the SARS-CoV-2 target includes a plurality of first primers, a plurality of second primers, and a plurality of detectable probes, wherein the plurality of first primers is the combination of a first primer comprising the oligonucleotide sequence selected from the group consisting of SEQ ID NOs: 1 and 27, and a first primer comprising the oligonucleotide sequence of SEQ ID NO: 5; wherein the plurality of second primers is the combination of a second primer comprising the oligonucleotide sequence of SEQ ID NO: 7 and a second primer comprising the oligonucleotide sequence of SEQ ID NO: 15; and wherein the plurality of detectable probes is the combination of an oligonucleotide probe comprising the oligonucleotide sequence of SEQ ID NO: 21 and an oligonucleotide probe comprising the oligonucleotide sequence selected from the group consisting of SEQ ID NOs: 25 and 32. In still another embodiment, the plurality of first primers is the combination of a first primer comprising the oligonucleotide sequence selected from the group consisting of SEQ ID NOs: 1 and 27, a first primer comprising the oligonucleotide sequence of SEQ ID NO: 5, and a first primer comprising the oligonucleotide sequence of SEQ ID NO: 6; the plurality of second primers is the combination of a second primer comprising the oligonucleotide sequence of SEQ ID NO: 7, a second primer comprising the oligonucleotide sequence of SEQ ID NO: 15, and a second primer comprising the oligonucleotide sequence of SEQ ID NO: 18; and the plurality of detectable probes is the combination of an oligonucleotide probe comprising the oligonucleotide sequence of SEQ ID NO: 21, an oligonucleotide probe comprising the oligonucleotide sequence selected from the group consisting of SEQ ID NOs: 25 and 32, and an oligonucleotide probe comprising the oligonucleotide sequence of SEQ ID NO: 26. In still another embodiment, the plurality of first primers is the combination of a first primer comprising the oligonucleotide sequence of SEQ ID NO: 27, and a first primer comprising the oligonucleotide sequence of SEQ ID NO: 40; the plurality of second primers is the combination of a second primer comprising the oligonucleotide sequence of SEQ ID NO: 7 and a second primer comprising the oligonucleotide sequence of SEQ ID NO: 41; and wherein the plurality of detectable probes is the combination of an oligonucleotide probe comprising the oligonucleotide sequence of SEQ ID NO: 42 and an oligonucleotide probe comprising the oligonucleotide sequence of SEQ ID NO: 43.

In another aspect, a method for simultaneously detecting SARS-CoV-2, influenza A, and influenza B in a sample is provided, comprising performing an amplifying step including contacting the sample with a first set of primers, a second set of primers, and a third set of primers, to produce one or more amplification products if SARS-CoV-2, and/or influenza A, and/or influenza B is present in the sample; wherein the first set of primers produces an amplification product if SARS-CoV-2 is present in the sample, the second set of primers produces an amplification product if influenza A is present in the sample, and the third set of primers produces an amplification product if influenza B is present in the sample; performing a hybridizing step including contacting the amplification product(s) with three or more detectable probes, wherein the three or more detectable probes includes at least one probe specific for the amplification products of each of the first, the second, and the third sets of primers; and detecting the presence or absence of the amplified products, wherein the presence of the amplified product is indicative of the presence of SARS-CoV-2, influenza A, and/or influenza B in the sample and wherein the absence of the amplified product is indicative of the absence of SARS-CoV-2, influenza A, and/or influenza B in the sample.

In one embodiment, the first set of primers used in the method(s) comprises a forward primer comprising or consisting of a first oligonucleotide sequence selected from the group consisting of SEQ ID NOs: 1-6, 27-31, 40, or a complement thereof; and a reverse primer comprising or consisting of a second oligonucleotide sequence selected from the group consisting of SEQ ID NOs: 7-20, and 41, or a complement thereof; and wherein the first detectable probe comprises or consists of a third oligonucleotide sequence selected from the group consisting of SEQ ID NOs: 21-26, 32 and 42-43 or a complement thereof.

In another embodiment, the first set of primers used in the method(s) comprises a forward primer comprising or consisting of an oligonucleotide sequence selected from the group consisting of SEQ ID NOs: 1-3 and 27-31, and a reverse primer comprising or consisting of an oligonucleotide sequence selected from the group consisting of SEQ ID NOs: 7-14; the second set of primers comprises a forward primer comprising or consisting of an oligonucleotide sequence of SEQ ID NO: 33, and a reverse primer comprising or consisting of an oligonucleotide sequence of SEQ ID NO: 34; and the third set of primers comprises a forward primer comprising or consisting of an oligonucleotide sequence of SEQ ID NO: 36, and a reverse primer comprising or consisting of an oligonucleotide sequence of SEQ ID NO: 37; and wherein the first detectable probe comprises or consists of an oligonucleotide sequence selected from the group consisting of SEQ ID NOs: 21-23, and 42, the second detectable probe comprises or consists of an oligonucleotide sequence of SEQ ID NO: 35 or 44, and the third detectable probe comprises or consists of an oligonucleotide sequence of SEQ ID NO: 38 or 45.

In another embodiment the method further comprises providing a fourth set of primers that produces an amplification product if SARS-CoV-2 or SARS-CoV-2 and other coronavirus target nucleic acids from the subgenus Sarbecovirus is present in the sample. In certain embodiments, the fourth set of primers comprises a forward primer comprising or consisting of an oligonucleotide sequence selected from the group consisting of SEQ ID NOs: 4-6, and 40, and a reverse primer comprising or consisting of an oligonucleotide sequence selected from the group consisting of SEQ ID NOs: 15-20, and 41; the fourth detectable probe comprises or consists of an oligonucleotide sequence selected from the group consisting of SEQ ID NOs: 24-26, 32 and 43.

In one embodiment, the first set of primers that produces an amplification product if SARS-CoV-2 is present in the sample comprises a forward primer comprising or consisting of an oligonucleotide sequence of SEQ ID NO: 27 and a reverse primer comprising or consisting of an oligonucleotide sequence of SEQ ID NO: 7 and the first detectable probe for detecting the amplification product comprises or consists of an oligonucleotide sequence of SEQ ID NO: 21 or 42. In another embodiment, the fourth set of primers that produces an amplification product if SARS-CoV-2 or SARS-CoV-2 and other coronavirus target nucleic acids from the subgenus Sarbecovirus is present in the sample comprises a forward primer comprising or consisting of an oligonucleotide sequence of SEQ ID NO: 5 or 40, and a reverse primer comprising or consisting of an oligonucleotide sequence of SEQ ID NO: 15 or 41, and the fourth detectable probe for detecting the amplification product comprises or consists of an oligonucleotide sequence of SEQ ID NO: 32 or 43.

Other embodiments provide an oligonucleotide comprising or consisting of a sequence of nucleotides selected from SEQ ID NOs: 1-45, or a complement thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs: 1-45, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 8 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

In one aspect, the specific SARS-CoV-2 probes may be labeled with a fluorescent dye which acts as a reporter. The probe may also have a second dye which acts as a quencher. The reporter dye is measured at a defined wavelength, thus permitting detection and discrimination of the amplified SARS-CoV-2 target. The fluorescent signal of the intact probes is suppressed by the quencher dye. During the PCR amplification step, hybridization of the probes to the specific single-stranded DNA template results in cleavage by the 5' to 3' nuclease activity of the DNA polymerase resulting in separation of the reporter and quencher dyes and the generation of a fluorescent signal. With each PCR cycle, increasing amounts of cleaved probes are generated and the cumulative signal of the reporter dye is concomitantly increased. Optionally, one or more additional probes (e.g., such as an internal reference control or other targeted probe (e.g., other viral nucleic acids) may also be labeled with a reporter fluorescent dye, unique and distinct from the fluorescent dye label associated with the SARS-CoV-2 probe. In such case, because the specific reporter dyes are measured at defined wavelengths, simultaneous detection and discrimination of the amplified SARS-CoV-2 target and the one or more additional probes is possible.

The present disclosure also provides for methods of detecting the presence or absence of SARS-CoV-2, or SARS-CoV-2 nucleic acid, in a biological sample from an individual. These methods can be employed to detect the presence or absence of SARS-CoV-2 or SARS-CoV-2 nucleic acid in nasopharyngeal (NSP) and oropharyngeal swab samples, for use in diagnostic testing. Additionally, the same test may be used by someone experienced in the art to assess other sample types to detect SARS-CoV-2 or SARS-CoV-2 nucleic acid. Such methods generally include performing a reverse transcription step and at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of SARS-CoV-2 or SARS-CoV-2 nucleic acid in the sample, and wherein the absence of binding is indicative of the absence of SARS-CoV-2 or SARS-CoV-2 nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of SARS-CoV-2 or SARS-CoV-2 nucleic acid.

In a further embodiment, a kit for detecting one or more nucleic acids of SARS-CoV-2 is provided. The kit can include one or more sets of primers specific for amplification of the gene target; and one or more detectable oligonucleotide probes specific for detection of the amplification products. In another embodiment, a kit for simultaneously detecting one or more nucleic acids of SARS-CoV-2, one or more nucleic acids of influenza A and one or more nucleic acids of influenza B is provided. The kit can include one or more sets or primers specific for amplification of the SARS-CoV-2 gene target, the influenza A gene target and the influenza B gene target, as well as one or more detectable oligonucleotide probes specific for detection of the amplification products for SARS-CoV-2, influenza A and influenza B.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of SARS-CoV-2 nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

FIG. 6 displays the summary of the Limit of Detection (LOD) Data from the experimental data shown in FIG. 5

FIG. 9.

DETAILED DESCRIPTION OF THE INVENTION

Figure 1:
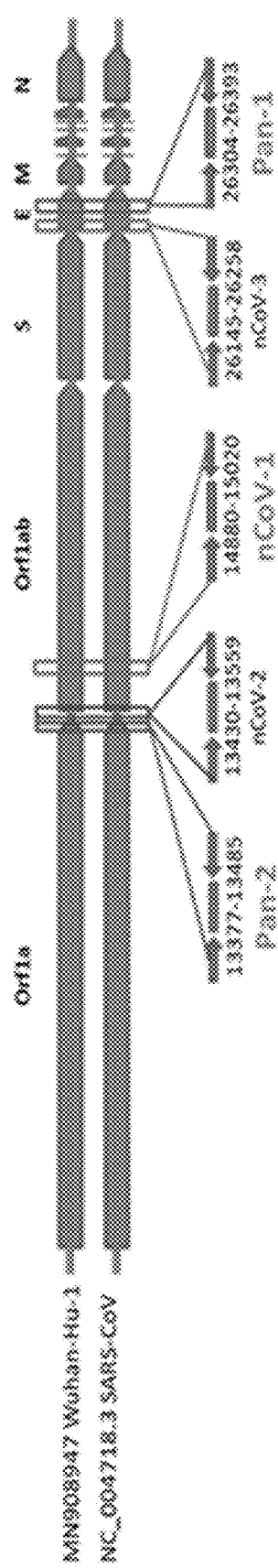
FIG. 1 shows the genome organization of SARS-CoV-2 (labeled here as Wuhan-Hu-1) and SARS-CoV and the locations of the target regions of the SARS-CoV-2 primer and probes of the present invention. E: envelope protein gene; M: membrane protein gene; N: nucleocapsid protein gene; ORF1a/b: ORF for non-structural genes; S: spike protein gene; Numbers below amplicon are genome position according to Wuhan-Hu-1, GenBank MN908947.

Diagnosis of SARS-CoV-2 infection by nucleic acid amplification provides a method for rapidly, accurately, reliably, specifically, and sensitively detecting the viral infection. A real-time reverse-transcriptase PCR assay for detecting SARS-CoV-2 in a non-biological or biological sample is described herein. Primers and probes for detecting SARS-CoV-2 are provided, as are articles of manufacture or kits containing such primers and probes. The increased specificity and sensitivity of real-time PCR for detection of SARS-CoV-2 compared to other methods, as well as the improved features of real-time PCR including sample containment and real-time detection of the amplified product, make feasible the implementation of this technology for routine diagnosis of SARS-CoV-2 infections in the clinical laboratory. Additionally, this technology may be employed for in vitro diagnostics as well as for prognosis. This SARS-CoV-2 detection assay may also be multiplexed with other assays for the detection of other nucleic acids, e.g., influenza virus, SARS-CoV, MERS-CoV, in parallel.

Furthermore, simultaneous diagnosis of SARS-CoV-2, influenza A and influenza B infection by nucleic acid amplification provides a method for rapidly, accurately, reliably, specifically, and sensitively detecting and differentiating these respiratory viral infections. A real-time reverse-transcriptase PCR assay for detecting and differentiating SARS-CoV-2, influenza A and influenza B in a non-biological or biological sample is described herein. Primers and probes for detecting SARS-CoV-2, influenza A, and influenza B are provided, as are articles of manufacture or kits containing such primers and probes. The increased specificity and sensitivity of real-time PCR for detection of SARS-CoV-2, influenza A, and influenza B compared to other methods, as well as the improved features of real-time PCR including sample containment and real-time detection of the amplified products, make feasible the implementation of this technology for routine diagnosis of SARS-CoV-2, influenza A, and influenza B infections in the clinical laboratory. Additionally, this technology may be employed for in vitro diagnostics as well as for prognosis. This SARS-CoV-2 detection multiplex assay may also be further multiplexed with other assays for the detection of other viral targets, e.g., influenza C virus, influenza D virus, SARS-CoV, or MERS-CoV, in parallel.

The SARS-CoV-2 genome is a positive sense single-stranded RNA molecule 29,903 bases in length (as shown in GenBank Accession No. MN908947) with the order of genes (5' to 3') as follows: replicase ORF1ab (21,291 bases with 16 predicted non-structural proteins that are essential for viral replication and viral assembly), spike (S gene, 3,822 bases coding for spike protein responsible for binding to cell receptor), ORF3ab (828 bases in length), envelope (E gene, 228 bases coding for envelope protein), membrane (M gene, 669 bases coding for membrane protein), nucleocapsid (N gene, 1260 bases coding for nucleocapsid protein that forms complexes with the genomic RNA). In addition, there is 265 bases of non-coding region at the 5' terminal end and 229 bases of non-coding region at the 3' terminal end.

The influenza A genome is a segmented negative sense single-stranded RNA molecule 13,588 bases in length (see www.ncbi.nlm.nih.gov/genomes/FLU/FLU.html). The genome is comprised of eight segments encoding between 10-14 genes, depending on the strain. From longest to shortest, the segments and the genes encoded thereon are: segment 1 (RNA polymerase subunit PB2); segment 2 (RNA polymerase subunit PB1 and PB1-F2 protein); segment 3 (RNA polymerase subunit PA and PA-X protein); segment 4 (hemagglutinin); segment 5 (nucleoprotein); segment 6 (neuraminidase); segment 7 (matrix protein M1 and matrix protein M2); and segment 8 (non-structural proteins NS1 and NEP). Hemagluttinin and neuraminidase are large proteins found on the exterior of the influenza virions. Hemagluttinin (HA) is responsible for binding of the influenza viral particles to the target cell and entry of the viral genome into the cell. Neuraminidase (NA) catalyzes release of virions from infected cells. There are 16 known subtypes of HA and nine of NA, but only H1, H2, and H3, and N1 and N2 are usually found in humans.

The influenza B genome, like the influenza A genome, is an eight-segmented negative sense single-stranded RNA molecule 14,548 bases in length. The genome of influenza B is very similar to that of influenza A, with a few exceptions. From longest to shortest, the segments and the genes encoded thereon are: segment 1 (RNA polymerase subunit PB2); segment 2 (RNA polymerase subunit PB1 protein); segment 3 (RNA polymerase subunit PA); segment 4 (hemagglutinin); segment 5 (nucleoprotein); segment 6 (neuraminidase and matrix protein NB); segment 7 (matrix protein M1 and membrane protein BM2); and segment 8 (non-structural proteins NS1 and NEP). Influenza B is less prevalent than influenza A in humans, but disproportionately affects children and adolescents.

The present disclosure includes oligonucleotide primers and fluorescent labeled hydrolysis probes that hybridize to the SARS-CoV-2 genome (e.g., at the ORF1ab gene and/or at the E gene), in order to specifically identify SARS-CoV-2 using, e.g., TaqMan® amplification and detection technology. The oligonucleotides specifically hybridize to the ORF1ab gene, and/or to the E gene. Having oligonucleotides that hybridize to multiple locations in the genome is advantageous for improved sensitivity compared to targeting a single copy genetic locus.

The disclosed methods may include performing a reverse transcription step and at least one cycling step that includes amplifying one or more portions of the nucleic acid molecule gene target from a sample using one or more pairs of primers. "SARS-CoV-2 primer(s)" as used herein refer to oligonucleotide primers that specifically anneal to nucleic acid sequences found in the SARS-CoV-2 genome, and initiate DNA synthesis therefrom under appropriate conditions producing the respective amplification products. Examples of nucleic acid sequences found in the SARS-CoV-2 genome, include nucleic acids within the ORF1ab gene, the S gene, the ORF3ab gene, the E gene, the M gene and the N gene and other predicted ORF regions. Each of the discussed SARS-CoV-2 primers anneals to a target region such that at least a portion of each amplification product contains nucleic acid sequence corresponding to the target. The one or more amplification products are produced provided that one or more nucleic acid is present in the sample, thus the presence of the one or more amplification products is indicative of the presence of SARS-CoV-2 in the sample. The amplification product should contain the nucleic acid sequences that are complementary to one or more detectable probes for SARS-CoV-2. "SARS-CoV-2 probe(s)" as used herein refer to oligonucleotide probes that specifically anneal to nucleic acid sequences found in the SARS-CoV-2 genome. Each cycling step includes an amplification step, a hybridization step, and a detection step, in which the sample is contacted with the one or more detectable SARS-CoV-2 probes for detection of the presence or absence of SARS-CoV-2 in the sample.

Similarly, the terms "influenza A primer(s)" and "influenza B primer(s)" as used herein refer to oligonucleotide primers that specifically anneal to nucleic acid sequences found in the influenza A genome and the influenza B genome, respectively, and initiate DNA synthesis therefrom under appropriate conditions, producing the respective amplification products. The terms "influenza A probe(s)" and "influenza B probe(s)" as used herein refer to oligonucleotide probes that specifically anneal to nucleic acid sequences found in the SARS-CoV-2 genome, and enable detection of the respective target amplification products.

As used herein, the term "amplifying" refers to the process of synthesizing nucleic acid molecules that are complementary to one or both strands of a template nucleic acid molecule (e.g., nucleic acid molecules from the SARS-CoV-2 genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-

410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Amplification and Detection of SARS-CoV-2

The present disclosure provides methods to detect SARS-CoV-2 by amplifying, for example, a portion of the SARS-CoV-2 nucleic acid sequence. Nucleic acid sequences of SARS-CoV-2 are available (e.g., GenBank Accession No. MN908947). Specifically, primers and probes to amplify and detect SARS-CoV-2 nucleic acid molecule targets are provided by the embodiments in the present disclosure.

For detection of SARS-CoV-2, primers and probes to amplify the SARS-CoV-2 are provided. SARS-CoV-2 nucleic acids other than those exemplified herein can also be used to detect SARS-CoV-2 in a sample. For example, functional variants can be evaluated for specificity and/or sensitivity by those of skill in the art using routine methods. Representative functional variants can include, e.g., one or more deletions, insertions, and/or substitutions in the SARS-CoV-2 nucleic acids disclosed herein.

More specifically, embodiments of the oligonucleotides each include a nucleic acid with a sequence selected from SEQ ID NOs:1-32 and 39, a substantially identical variant thereof in which the variant has at least, e.g., 80%, 90%, or 95% sequence identity to one of SEQ ID NOs: 1-32 and 39, or a complement of SEQ ID NOs: 1-32 and 39 and the variant.

TABLE 1

SARS-CoV-2 Forward Primers
Forward Primers

| Oligo Name | SEQ ID NO: | Sequence | Modifications |
| --- | --- | --- | --- |
| NCOV-1F.A | 1 | TGATTGTTACGATGGTGGCTGTJ | J = t-butylbenzyl dA |
| NCOV-1-FN1.A | 27 | CTTTGATTGTTACGATGGTGGCTGTATTAJ | J = t-butylbenzyl dA |
| NCOV-1-FN3.A | 28 | TACTTTGATTGTTACGATGGTGGCTGTJ | J = t-butylbenzyl dA |
| NCOV-2-FN2.A | 29 | TACTTTGATTGTTACGATGGTGGCTGTATTJ | J = t-butylbenzyl dA |
| NCOV-4-FN4.A | 30 | TTGTTACGATGGTGGCTGTATTAATGCTJ | J = t-butylbenzyl dA |
| NCOV-4-FN5.A | 31 | GATGGTGGCTGTATTAATGCTAACCAJ | J = t-butylbenzyl dA |
| NCOV-F.core | 39 | TTGTTACGATGGTGGCTGTA | |
| NCOV-N3-F3.A | 40 | TTTTACACTTAAAAACACAGTCTGTACCGTK | K = t-butylbenzyl dC |
| NCOV-2F | 2 | TTCATCCGGAGTTGTTAATCCAGTJ | J = t-butylbenzyl dA |
| NCOV-3F.A | 3 | CCCATGCTTCAGTCAGCTGJ | J = t-butylbenzyl dA |
| SARBV-1F.A | 4 | TCTTGCTTTCGTGGTATTCTTGCTJ | J = t-butylbenzyl dA |

TABLE 1-continued

SARS-CoV-2 Forward Primers
Forward Primers

| Oligo Name | SEQ ID NO: | Sequence | Modifications |
| --- | --- | --- | --- |
| SARBV-1F2.A | 5 | GAACTTATGTACTCATTCGTTTCGGAJ | J = t-butylbenzyl dA |
| SARBV-2F.A | 6 | CCGTCTGCGGAATGTGGAJ | J = t-butylbenzyl dA |

TABLE 2

SARS-CoV-2 Reverse Primers
Reverse Primers

| Oligo Name | SEQ ID NO: | Sequence | Modifications |
| --- | --- | --- | --- |
| NCOV-1R.A | 7 | AGTGCATCTTGATCCTCATAACTCJ | J = t-butylbenzyl dA |
| NCOV-1R1.A | 8 | GCATCTTGATCCTCATAACTCATTGAATCJ | J = t-butylbenzyl dA |
| NCOV-1R2.A | 9 | ACTCATTGAATCATAATAAAGTCTAGCCTTJ | J = t-butylbenzyl dA |
| NCOV-2R | 10 | ACGAATGAGTACATAAGTTCGTACTCJ | J = tbutylbenzyl dA |
| NCOV-2R1.A | 11 | TCTCTTCCGAAACGAATGAGTACJ | J = tbutylbenzyl dA |
| NCOV-2R2.A | 12 | CCTGTCTCTTCCGAAACGAATGJ | J = tbutylbenzyl dA |
| NCOV-3R1.A | 13 | GCAAAACCAGCTACTTTATCATTGTAGJ | J = tbutylbenzyl dA |
| NCOV-3R2.A | 14 | TCATTGTAGATGTCAAAAGCCCTGTATJ | J = tbutylbenzyl dA |
| NCOV-N3-R1.A | 41 | AACCCGTTTAAAAACGATTGTGCATCJ | J = tbutylbenzyl dA |
| SARBV-1R.A | 15 | CTCACGTTAACAATATTGCAGCAGTJ | J = tbutylbenzyl dA |
| SARBV-1R1.A | 16 | AACTCACGTTAACAATATTGCAGCJ | J = tbutylbenzyl dA |
| SARBV-1R2.A | 17 | GTTTTACTAGACTCACGTTAACAATATTGCJ | J = tbutylbenzyl dA |
| SARBV-2R.A | 18 | ACTTACACCGCAAACCCGTTTJ | J = tbutylbenzyl dA |
| SARBV-2R1.A | 19 | GTGCCGCACGGTGTAAGJ | J = tbutylbenzyl dA |
| SARBV-2R2.A | 20 | GTGTAAGACGGGCTGCACTTJ | J = tbutylbenzyl dA |

TABLE 3

SARS-CoV-2 Probes
Probes

| Oligo Name | SEQ ID NO: | Sequence | Modifications |
|---|---|---|---|
| WUHAN-4P | 21 | FTCATCGQTCAACAACCTAGACAAA TCAGCTGGTTTTCSp | Sp = Spacer-C3, F = FAM, Q = BHQ2 |
| NCOV-2P | 22 | FCGACGACGQACTACTAGCGTGCC TTTGTAAGCSp | Sp = Spacer-C3, F = FAM, Q = BHQ2 |
| NCOV-3P8Q | 23 | FCGTGCGGCQACAGGCACTAGTAC TGATGTCGSp | Sp = Spacer-C3, F = FAM, Q = BHQ2 |
| NCOV-4P-JA270-Q10.P | 42 | <JA>TCATCGTCAAQCAACCTAGAC AAATCAGCTGGTTTTCSp | Sp = Spacer-C3, <JA> = JA270-Thr, Q = BHQ2 |
| NCOV-N3-JA | 43 | <JA>TCCGCGAACCCAQTGCTTCAG TCAGCTGATSp | Sp = Spacer-C3, <JA> = JA270-Thr, Q = BHQ2 |
| SARBV-P1 | 24 | HAGCCATCCQTTACTGCGCTTCGAT TGTGTGCSp | Sp = Spacer-C3, H = HEX-Thr, Q = BHQ2 |
| SARBV-P1_6Q.P | 25 | HAGCCATQCCTTACTGCGCTTCGAT TGTGTGCP | P = Phosphate, H = HEX-Thr, Q = BHQ2 |
| SARBV-P1-N2_6Q.C3 | 32 | HATCCTTQACTGCGCTTCGATTGTG TGCGTASp | Sp = Spacer-C3, H = HEX-Thr, Q = BHQ2 |
| SARBV-P2 | 26 | HATGGCTGQTAGTTGTGACCAACT CCGCGAACSp | Sp = Spacer-C3, H = HEX-Thr, Q = BHQ2 |

In one embodiment, the above-described sets of SARS-CoV-2 primers and probes are used in order to provide for detection of SARS-CoV-2 in a biological sample suspected of containing SARS-CoV-2 (Tables 1-3). The sets of primers and probes may comprise or consist of the primers and probes specific for the SARS-CoV-2 nucleic acid sequences, comprising or consisting of the nucleic acid sequences of SEQ ID NOs: 1-32 and 39. In another embodiment, the primers and probes for the SARS-CoV-2 target comprise or consist of a functionally active variant of any of the primers and probes of SEQ ID NOs: 1-32 and 39.

A functionally active variant of any of the primers and/or probes of SEQ ID NOs: 1-32 and 39 may be identified by using the primers and/or probes in the disclosed methods. A functionally active variant of a primer and/or probe of any of the SEQ ID NOs: 1-32 and 39 pertains to a primer and/or probe that provide a similar or higher specificity and sensitivity in the described method or kit as compared to the respective sequence of SEQ ID NOs: 1-32 and 39.

The variant may, e.g., vary from the sequence of SEQ ID NOs: 1-32 and 39 by one or more nucleotide additions, deletions or substitutions such as one or more nucleotide additions, deletions or substitutions at the 5' end and/or the 3' end of the respective sequence of SEQ ID NOs: 1-32 and 39. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the SARS-CoV-2 target, e.g., nucleic acids encoding alternative portions of SARS-CoV-2 can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of SARS-CoV-2. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a SARS-CoV-2 (target) nucleic acid. A "probe" can be referred to as a "detection probe" meaning that it detects the target nucleic acid.

In some embodiments, the described SARS-CoV-2 probes can be labeled with at least one fluorescent label. In one embodiment, the SARS-CoV-2 probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs: 21-26 and 32.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of SARS-CoV-2 primers and probes nucleic acid molecules. Constructs can be used, for example, as control template nucleic acid molecules. Vectors suitable for use are commercially available and/or produced by recombinant nucleic acid technology methods routine in the art. SARS-CoV-2 nucleic acid molecules can be obtained, for example, by chemical synthesis, direct cloning from SARS-CoV-2, or by nucleic acid amplification.

Constructs suitable for use in the methods typically include, in addition to the SARS-CoV-2 nucleic acid molecules (e.g., a nucleic acid molecule that contains one or more sequences of SEQ ID NOs: 1-32 and 39), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing SARS-CoV-2 nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Amplification and Detection of Influenza A and Influenza B

The present disclosure also provides methods to simultaneously detect SARS-CoV-2, influenza A and influenza B by amplifying a portion of the SARS-CoV-2 nucleic acid sequence, a portion of the influenza A nucleic acid sequence, and a portion of the influenza B nucleic acid sequence. Primers and probes to amplify and detect SARS-CoV-2 nucleic acid molecule targets were described in the previous section. Nucleic acid sequences of influenza A and influenza B are available in GenBank Accession No. KC781450 (A/Michigan/01/2010(H1N1) and KM654608 (B/Connecticut/Flu103/2013), respectively. Specifically, primers and probes to amplify and detect influenza A and influenza B nucleic acid molecule targets are provide by the embodiments in the present disclosure. FIGS. 9B and 9C show the locations targeted by the influenza A primers and probes (SEQ ID NOs: 33-35 and 44 targeting the segment 7 M1 and M2 genes) and by the influenza B primers and probes (SEQ ID NOs: 36-38 and 45 targeting the segment 8 NEP and NS1 genes).

More specifically, embodiments of the oligonucleotides each include a nucleic acid with a sequence selected from SEQ ID NOs: 33-35 and 44 for influenza A, a substantially identical variant thereof in which the variant has at least, e.g., 80%, 90%, or 95% sequence identity to one of SEQ ID NOs: 33-35 and 44 or a complement of SEQ ID NOs: 33-35, and 44, and the variant; or selected from SEQ ID NOs: 36-38 and 45 for influenza B, a substantially identical variant thereof in which the variant has at least, e.g., 80%, 90%, or 95% sequence identity to one of SEQ ID NOs: 36-38 and 45, or a complement of SEQ ID NOs: 36-38 and 45, and the variant.

TABLE 4

Influenza A and Influenza B Primers and Probes

| Oligo Name | SEQ ID NO: | Sequence | Modifications |
|---|---|---|---|
| Influenza A Primers and Probes | | | |
| FLUAF M1 121 146 (forward primer) | 33 | GCTCTCATGGAATGGCTAAAGAC AJ | J = t-butylbenzyl dA |
| FLUA_RP4_A (reverse primer) | 34 | TGGACAAAGCGTCTACGK | K = t-butylbenzyl dC |
| FLUAP.H.C3_M1_ 212_181.6COU1.C (probe) | 35 | <COU>CACTGGQGCACGGTGAGC GTGAACACAAATCCSp | Sp = Spacer-C3, <COU> = Coumarin-Thr, Q = BHQ2 |

TABLE 4-continued Influenza A and Influenza B Primers and Probes

| Oligo Name | SEQ ID NO: | Sequence | Modifications |
|---|---|---|---|
| FLUAP.H.C3_M1_212_181.6 (probe) | 44 | \<HEX\>CACTGGQGCACGGTGAGC GTGAACACAAATCCSp | Sp = Spacer-C3, \<HEX\> = HEX-Thr, Q = BHQ2 |

Influenza B Primers and Probes

| Oligo Name | SEQ ID NO: | Sequence | Modifications |
|---|---|---|---|
| FLUBF_NS1.749 770 (forward primer) | 36 | AAGATGGCCATCGGATCCTCAJ | J = tbutylbenzyl dA |
| FLUBR_NS1.865_8 42 (reverse primer) | 37 | GGTGCTCTTGACCAAATTGGGATJ | J = tbutylbenzyl dA |
| FLUB_PRB2_11Q_JA270.C3 (probe) | 38 | \<JA\>CATTCAAAGCCQAATTCGAG CAGCTGAAACTGCSp | Sp = Spacer-C3, \<JA\> = JA270_Thr, Q = BHQ2 |

Influenza A Primers and Probes

| Oligo Name | SEQ ID NO: | Sequence | Modifications |
|---|---|---|---|
| FLUB_THRBP2_K 77 (probe) | 45 | QC\<D_LNA_A\>TTCAAAG\<DBCO\> CCAATTCGAGCAGCTGAAACTGC Sp | Sp = Spacer-C3, \<D_LNA_A\> = A with D-locked nucleic acid; \< DBCO\> = dibenzocycloocty-Thr, Q = BHQ2 |

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described SARS-CoV-2 nucleic acid sequences (e.g., SEQ ID NOs: 1-20, 27-31). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, such as SARS-CoV-2 as well as other flaviviruses, is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ SARS-CoV-2 nucleic acid such as RNA or DNA (cDNA). The template nucleic acid need not be purified; it may be a minor fraction of a complex mixture, such as SARS-CoV-2 nucleic acid contained in human cells. SARS-CoV-2 nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs: 1-20, 27-31) are combined with PCR reagents under reaction conditions that induce primer extension. For example, chain extension reactions generally include 50 mM KCl, 10 mM Tris-HCl (pH 8.3), 15 mM MgCl$_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target SARS-CoV-2 nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety (e.g., HEX) and a corresponding quencher (e.g., BlackHole Quenchers™ (BHQ)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the SARS-CoV-2 target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of Amplification Products

The present disclosure provides methods for detecting the presence or absence of SARS-CoV-2 in a biological or non-biological sample. Methods provided avoid problems of sample contamination, false negatives, and false positives. The methods include performing a reverse transcription step and at least one cycling step that includes amplifying a portion of SARS-CoV-2 target nucleic acid molecules from a sample using one or more pairs of SARS-CoV-2 primers, and a FRET detecting step. Multiple cycling steps are performed, preferably in a thermocycler. Methods can be performed using the SARS-CoV-2 primers and probes to detect the presence of SARS-CoV-2, and the detection of SARS-CoV-2 indicates the presence of SARS-CoV-2 in the sample.

As described herein, amplification products can be detected using labeled hybridization probes that take advantage of FRET technology. One FRET format utilizes TaqMan® technology to detect the presence or absence of an amplification product, and hence, the presence or absence of SARS-CoV-2. TaqMan® technology utilizes one single-stranded hybridization probe labeled with, e.g., one fluorescent dye (e.g., HEX) and one quencher (e.g., BHQ), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of SARS-CoV-2 in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of SARS-CoV-2 genomes). If amplification of SARS-CoV-2 target nucleic acid occurs and an amplification product is produced, the step of hybridizing results in a detectable signal based upon FRET between the members of the pair of probes.

Generally, the presence of FRET indicates the presence of SARS-CoV-2 in the sample, and the absence of FRET indicates the absence of SARS-CoV-2 in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to respiratory specimens (nasopharyngeal and oropharyngeal swabs), urine, fecal specimens, blood specimens, plasma, dermal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release SARS-CoV-2 nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the SARS-CoV-2 probes from the SARS-CoV-2 amplification products can confirm the presence or absence of SARS-CoV-2 in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect SARS-CoV-2. An article of manufacture can include primers and probes used to detect the SARS-CoV-2 gene target, together with suitable packaging materials. Representative primers and probes for detection of SARS-CoV-2 are capable of hybridizing to SARS-CoV-2 target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to SARS-CoV-2 target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the SARS-CoV-2 probes. Examples of suitable FRET donor fluorescent moieties and corresponding acceptor fluorescent moieties are provided above.

Articles of manufacture can also contain a package insert or package label having instructions thereon for using the SARS-CoV-2 primers and probes to detect SARS-CoV-2 in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

Example 1: SARS-CoV-2 Assay Description

A real-time Reverse Transcription-Polymerase Chain Reaction (RT-PCR) test was developed on the Cobas® 6800/8800 Systems that allows for the qualitative detection of nucleic acids from the SARS-CoV-2 in nasopharyngeal (NSP) and oropharyngeal swab samples from patients who meet the CDC clinical criteria. The assay detects: (i) specific nucleic acid sequences from the non-structural Open Reading Frame (ORF1a/b) in the genome of the SARS-CoV-2 in one channel and (ii) the conserved sequences in the structural Envelope (E) gene location common to all Sarbecoviruses including SARS-CoV-2, in a different channel. Results are for the specific detection of SARS-CoV-2 RNA that are detectable in nasopharyngeal and oropharyngeal swab samples during the acute phase of infection.

Nucleic acid from patient samples and added RNA-Internal Control molecules (same as the existing RNA QS reagent) are simultaneously extracted. Viral nucleic acids are released by addition of proteinase and lysis reagent to the sample. The released nucleic acid binds to the silica surface of the added magnetic glass particles. Unbound substances and impurities, such as denatured proteins, cellular debris and potential PCR inhibitors are removed with subsequent wash reagent steps and purified nucleic acid is eluted from the magnetic glass particles with elution buffer at elevated temperature.

Example 2: SARS CoV-2 Assay Design Strategy

The diagnostic test was designed for the detection of a novel coronavirus (SARS-CoV-2) that is classified under the family Coronavirus, genus Betacoronavirus and subgenus Sarbecovirus (Lu et al, Lancet, 2020, (20) 30251-8). This coronavirus is novel and it is not known what regions are subject to variation or recombination. Given the infancy of the knowledge on this virus, a single analyte dual-target assay was designed for the specific detection of nucleic acid sequences of SARS-CoV-2 in the FAM channel, and Sarbecovirus subgenus family that includes SARS-CoV-2, in the HEX channel. SARS-CoV-2 is closely related to SARS-CoV with genomic similarities.

Sequences were downloaded from the NCBI and the Global Initiative on Sharing All Influenza Data (GISAID) databases. There were seven sequences downloaded from the GISAID database.

Sequences from the subgenus Sarbecovirus (taxonomy ID 2509511) were downloaded from the NCBI database. There were 1,094 sequences >200 bases in length. At this time, the NCBI classified the SARS-CoV-2 as "Wuhan seafood market pneumonia virus" and there was no taxonomy ID assigned. To create the inclusivity group for SARS-CoV-2, these sarbecovirus sequences were inspected to identify viruses labelled as "Wuhan seafood market pneumonia virus". Seven sequences were available and used to identify seven target regions in six non-overlapped regions. The conserved nature of the region was assessed by comparing to other Sarbecoviruses and then selecting regions in the ORF1a non-structural region that were unique to SARS-CoV-2. For the pan-Sarbecovirus detection, a conserved region in the structural protein Envelope E-gene and also a conserved ORF1a/b region were chosen. The pan-Sarbecovirus detection sets could also detect the novel SARS-CoV-2 virus. This dual-target design strategy was taken over a single target because of the limited sequence availability and understanding of this new viruses stability over time. Selective amplification of an RNA Internal Control was achieved by the use of non-competitive sequence specific forward and reverse primers that have no homology with the coronavirus genome. A thermostable DNA polymerase enzyme was used for amplification.

Monitoring the NCBI and GISAID databases, newly available sequences were downloaded capturing taxonomy ID, country and sample collection and sequence deposition dates, where available. These sequences were collected from China, USA, England, Australia, Japan, Italy, Germany, Finland, France, Nepal, Taiwan, Singapore, and South Korea. There were 175 sequences available between the two databases, and the sequences were identical in the SARS-CoV-2 assay target regions for all available virus sequences except one. MT039890 had a single nucleotide polymorphism (SNP) near the 3'-end of the probe hybridization site which should have no impact to performance of the assay.

Example 3: Selection of SARS-CoV-2 Primer and Probe Oligonucleotides

A master mix was provided that contains detection probes which are specific for the coronavirus type SARS-CoV-2, members of the Sarbecovirus subgenus, and the RNA Internal Control nucleic acid, respectively. The coronavirus and RNA Internal Control detection probes were each labeled with unique fluorescent dyes, which act as a reporter. Each probe also contained a second dye which acts as a quencher. PCR Primers for amplifying the region of interest were designed with effort made to avoid reported SNPS in the target regions. Thus, studies were initiated with a single well assay design that detected SARS-CoV-2 using: (i) Specific nucleic acid sequences from the non-structural Open Reading Frame (ORF1a/b) in the genome of the SARS-CoV-2 in one channel (FAM) (nCoV1 assay) and (ii) Conserved sequences in ORF-1 and structural Envelope (E) Gene location common to all other Sarbecoviruses including SARS-CoV-2 using two pan-Sarbecovirus assays in a different channel (HEX) (pan-1 and/or pan-2) to provide a high degree of robustness. The relative locations of the amplicon targets on the SARS-CoV-2 genome compared to their locations on the SARS-CoV genome are shown on FIG. 1. A bioinformatics analysis of the SARS-CoV-2 assays that could be multiplexed with GIC oligonucleotides that are used for detection of the process control was done to screen initial assays for performance. Select combination set of primers and probes are shown in Table 5.

TABLE 5

Assay and Oligonucleotides Screened

| Assay Name | Target Gene | Oligo Name | SEQ ID NO: |
|---|---|---|---|
| nCoV1 | ORF1a/b | NCOV-1F.A | 1 |
|  |  | NCOV-1R.A | 7 |
|  |  | WUHAN-4P.P | 21 |
| Pan-Sarbeco-2 | ORF1a/b | SARBV-2F.A | 6 |
|  |  | SARBV-2R.A | 18 |
|  |  | SARBV-P2.P | 26 |
| Pan-Sarbeco-1 | Envelope | SARBV-1F.A | 4 |
|  |  | SARBV-1F2.A | 5 |
|  |  | SARBV-1R.A | 15 |
|  |  | SARBV-P1 | 24 |
|  |  | SARBV-P1_6Q.P | 25 |

Example 4: PCR Assay Reagents and Conditions

Real-time PCR detection of SARS-CoV-2 was performed using the Cobas® 6800/8800 systems platforms (Roche Molecular Systems, Inc., Pleasanton, Calif.). The final concentrations of the amplification reagents are shown below:

TABLE 6

PCR Amplification Reagents

| Master Mix Component | Final Conc (50 uL) |
|---|---|
| DMSO | 0-5.4 % |
| NaN3 | 0.027-0.030 % |
| Potassium acetate | 120.0 mM |
| Potassium hydroxide | 19.2 uM |
| Glycerol | 3.0 % |
| Tween 20 | 0.015 % |
| EDTA | 43.9 uM |
| Tricine | 60.0 mM |
| Aptamer | 0.222 uM |
| UNG Enzyme | 5.0-10.0 U |
| Z05-SP-PZ Polymerase | 30.0-45.0 U |
| dATP | 400.0 uM |
| dCTP | 400.0 uM |
| dGTP | 400.0 uM |
| dUTP | 800.0 uM |

TABLE 6-continued

PCR Amplification Reagents

| Master Mix Component | Final Conc (50 uL) |
|---|---|
| Forward primer oligonucleotides | 0.30 µM |
| Reverse primer oligonucleotides | 0.30-0.40 µM |
| Probe oligonucleotides | 0.15 µM |

The following table shows the typical thermoprofile used for PCR amplification reaction:

TABLE 7

PCR Thermoprofile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
| | 94 | None | 00:00:05 | 4.4 | | |
| | 55 | None | 00:02:00 | 2.2 | | |
| | 60 | None | 00:06:00 | 4.4 | | |
| | 65 | None | 00:04:00 | 4.4 | | |
| 1st Measurement | 95 | None | 00:00:05 | 4.4 | 5 | Quantification |
| | 55 | Single | 00:00:30 | 2.2 | | |
| 2nd Measurement | 91 | None | 00:00:05 | 4.4 | 45 | Quantification |
| | 58 | Single | 00:00:25 | 2.2 | | |
| Cooling | 40 | None | 00:02:00 | 2.2 | 1 | None |

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Example 5: Performance Assessment of SARS-CoV-2 Test

Assessment of components, workflows and assay reagents for the SARS-CoV-2 test were performed using the Cobas® 6800 reagents. Linearized recombinant plasmids were tested with the assay oligonucleotides to assess performance. In vitro transcripts were also generated to evaluate performance of the assays using synthetic RNA. Nucleic acid quantitation was done using Qubit with DNA and RNA standards. Plasmid DNA and transcripts were serially diluted in MultiPrep Specimen Diluent Buffer (also known as Bulk Generic Specimen Diluent) and used in assay performance studies. Internal control oligonucleotides (generic internal control, GIC) were included in the evaluations with both linearized DNA and RNA transcripts. Experiments were conducted on the Roche LC480 Cycler that was fitted and calibrated with the Cobas® 6800 filters using the Cobas® 6800 generic Thermocycling profile. Nasopharyngeal (NSP) samples were obtained from patients exhibiting upper respiratory symptoms using flocculated swabs and collected in Universal Viral Transport Medium (3 mL). A modified sample preparation workflow (Process and Elute, PnE) was used on the Cobas® 6800 System wherein either 300 or 400 µL of NSP sample was processed to prepare nucleic acid eluates. These eluates contain the gIC armored RNA (QS RNA Control) that follow the same NSP sample preparation process on the Cobas® 6800 and serves as the internal sample processing control. Eluates were then used in studies with the SARS-CoV-2 assays with amplification and detection on the LC480 and/or the Cobas® 6800 analytical cycler.

Figure 2:
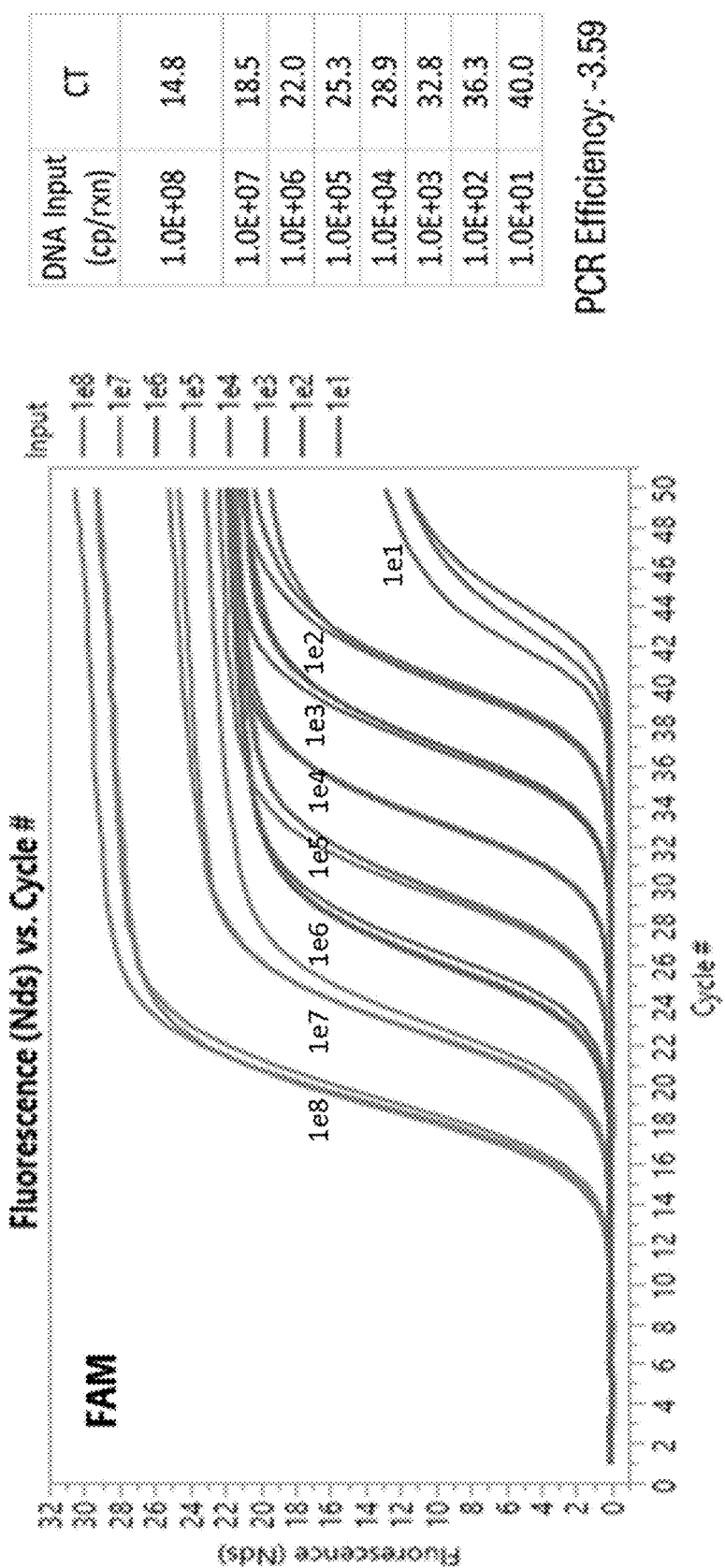
FIG. 2 shows PCR growth curves of experiments where the primers and probes for the nCoV1 assay are tested against various concentrations of linearized SARS-CoV-2 DNA template.
Figure 3:
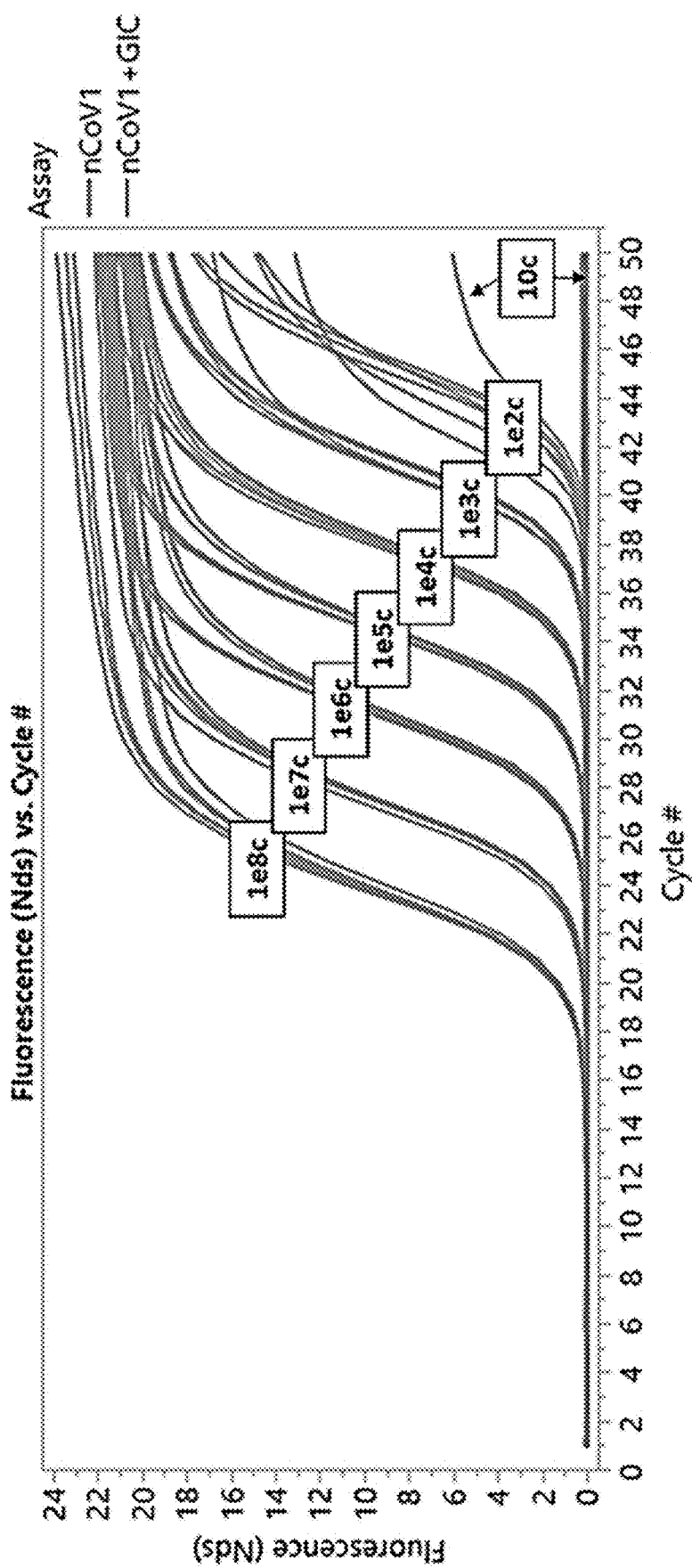
FIG. 3 shows PCR growth curves of experiments where the primers and probes for the nCoV1 assay are tested against various concentrations of RNA transcript of SARS-CoV-2.
Figure 4:
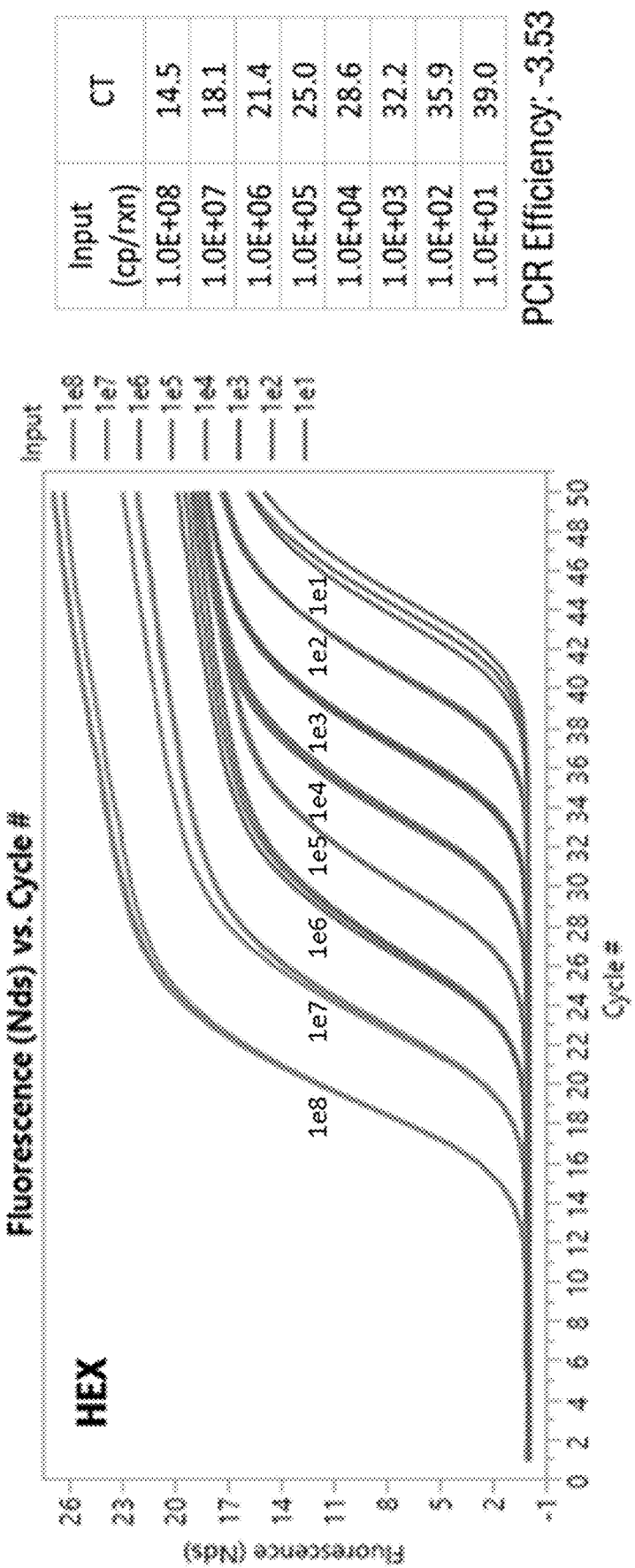
FIG. 4 shows PCR growth curves of experiments where the primers and probes for the Pan-Sarbeco-2 assay are tested against various concentrations of linearized SARS-CoV-2 DNA template.

Assay oligonucleotides were first evaluated in singleplex assays. The performance of the nCoV1 singleplex assay (SEQ ID NOs: 1, 7, 21) with linearized recombinant plasmid with the target sequence from 1.0E+8 copies (cp) down to 1.0E+01 cp per PCR reaction represented as growth curves and average CT (n=3 replicates) is shown in FIG. 2. The nCov1 assay exhibited good sensitivity with detection down to 10 copies of target sequence per PCR reaction. The assay was also evaluated with in vitro transcripts and the data is shown in FIG. 3. Here, the assay exhibited good sensitivity with detection down to 100 copies of target transcript per PCR reaction with and without the gIC assay with acceptable dynamic range and PCR efficiency with synthetic RNA transcripts. The Pan-Sarbeco-2 assay (SEQ ID NOs: 6, 18, 26) was evaluated next using linearized plasmid DNA as well as transcripts to determine the sensitivity of the assays and the results are shown in FIG. 4.

Figure 5:
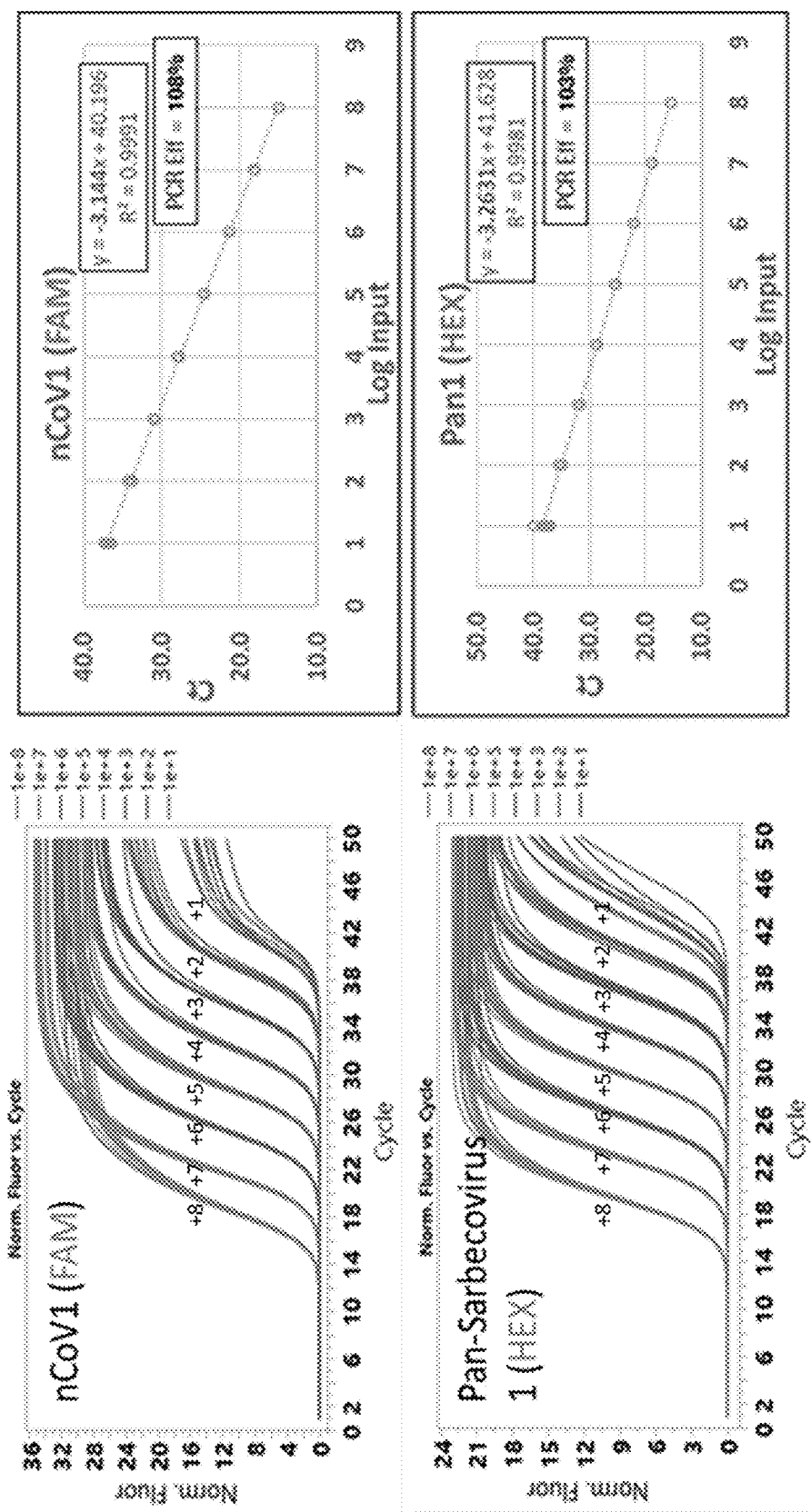
FIG. 5 shows the growth curves (left) and Ct charts with dynamic range plotted (right) in the multiplex PCR test described in Example 5 for the nCoV1 assay (top) and the Pan-Sarbecovirus-1 assay (bottom) and across the indicated levels (1e+8 to 1e+1) tested using the synthetic in vitro transcripts.

Multiplex PCR assays were then performed in which the primers and probe oligonucleotides of the nCoV1 assay (SEQ ID NOs: 1, 7, 21), the primers and probe oligonucleotides of the Pan-1 assay (SEQ ID NOs: 5, 15, 25) were tested in a single reaction. Recombinant plasmids containing SARS-CoV-2 and Sarbecovirus target regions (i.e. ORF1a/b and Envelope genes, respectively) were used to generate in vitro transcripts (250 and 261 bases). RNA was quantified on the Qubit fluorimeter with RNA standards provided with the assay. To cover a wide dynamic range, serial dilutions of the transcript stock were prepared at 10-fold concentration levels between 1e8 and 1e1 copies (cp)/PCR in specimen diluent (SD=Tris Buffer) that contains carrier RNA and tested in replicates of 10. PCR was set up manually using the generic Cobas® 6800/8800 mastermix with the added test primers and probes with amplification and detection on the LightCycler® 480 (LC480) thermocycler fitted with the Cobas® 6800/8800 filters. Shown in FIG. 5 are the growth curves and Ct charts with dynamic range plotted for the two targets across the levels tested using synthetic in vitro transcripts.

The data indicate robust growth curves and PCR efficiency over a wide dynamic range with transcripts detected down to 10 copies per PCR reaction for both targets. The initial Limit of Detection (LOD) study data is summarized in FIG. 6, which shows 100% hit rate at levels down to 10 copies/PCR reaction in the specimen diluent sample.

Example 6: Assay Performance of SARS-CoV-2 Test Using Patient Sample Isolate

Whole genome viral RNA was isolated from BEI SARS-CoV-2 Isolate USA-WA1/2020 (2.8E+5 $TCID_{50}$/mL) using a Qiagen virus sample preparation protocol. Assuming 100% genomic RNA recovery in the eluate, serial ten-fold dilutions were prepared from 2.8E+5 $TCID_{50}$/mL down to 2.80E-02 $TCID_{50}$/mL (7 levels). Final dilutions were made by spiking 5 µL of purified RNA into 20 µL (~$5.6e^{+3}$, $5.6e^{+2}$, $5.6e^{+1}$, $5.6e^{+0}$, $5.6e^{-1}$, $5.6e^{-2}$, $5.6e^{-3}$ TCID$_{50}$/mL) of one of the following two matrices: a) Cobas® specimen diluent buffer/Tris buffer (SD) with 10 replicates at lower levels and 3 replicates in the upper 3 levels, and b) Cobas® 6800/8800 system eluate prepared from clinical nasopharyngeal swab specimens from subjects with upper respiratory infection symptoms, (NSP) Nasopharyngeal Swab Specimen Eluate (NSP) with 2 replicates. RNA transcripts in Cobas® SD were included as control.

Figure 7:
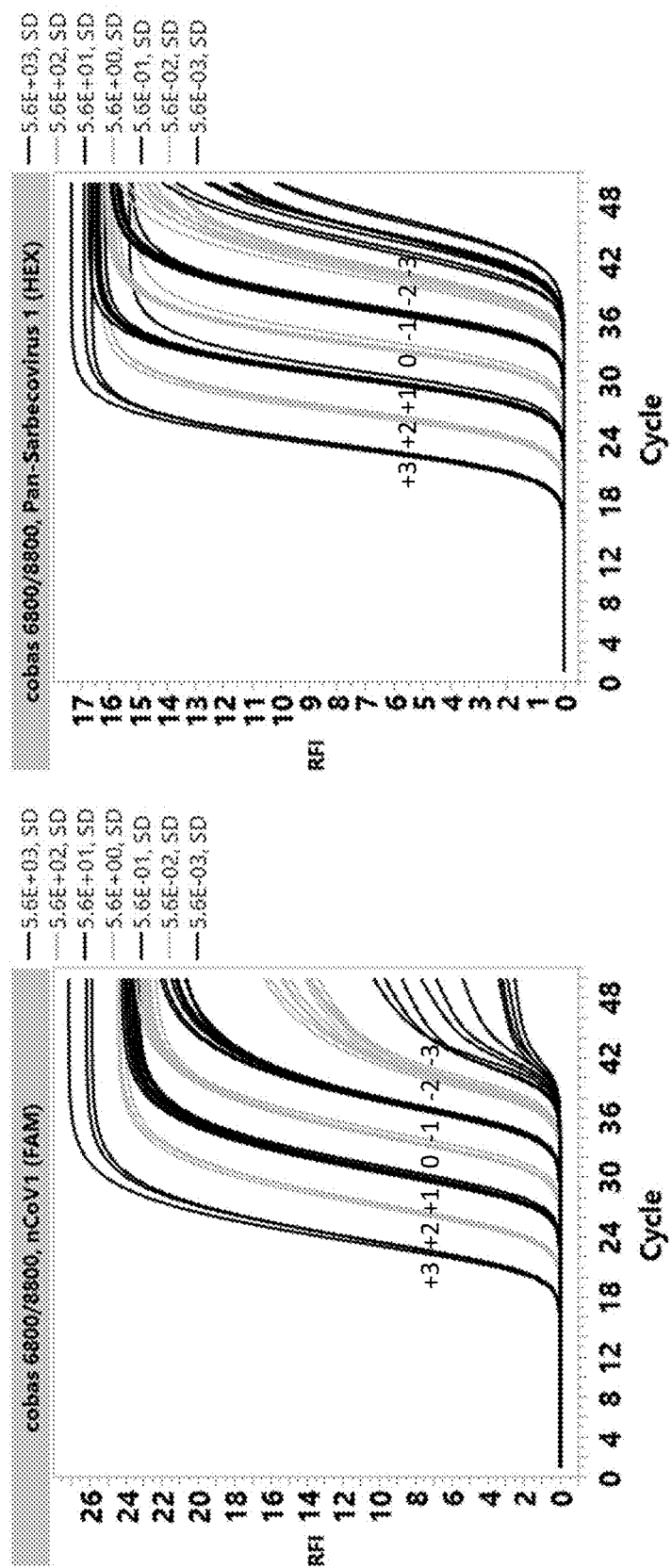
FIG. 7 shows the growth curves generated from the SARS-CoV-2 Test using isolated genomic RNA from a patient sample at the indicated levels diluted in Specimen Diluent (SD) in a multiplex PCR test comprising the nCoV1 assay (left) and Pan-Sarbecovirus-1 assay (right).
Figure 8:
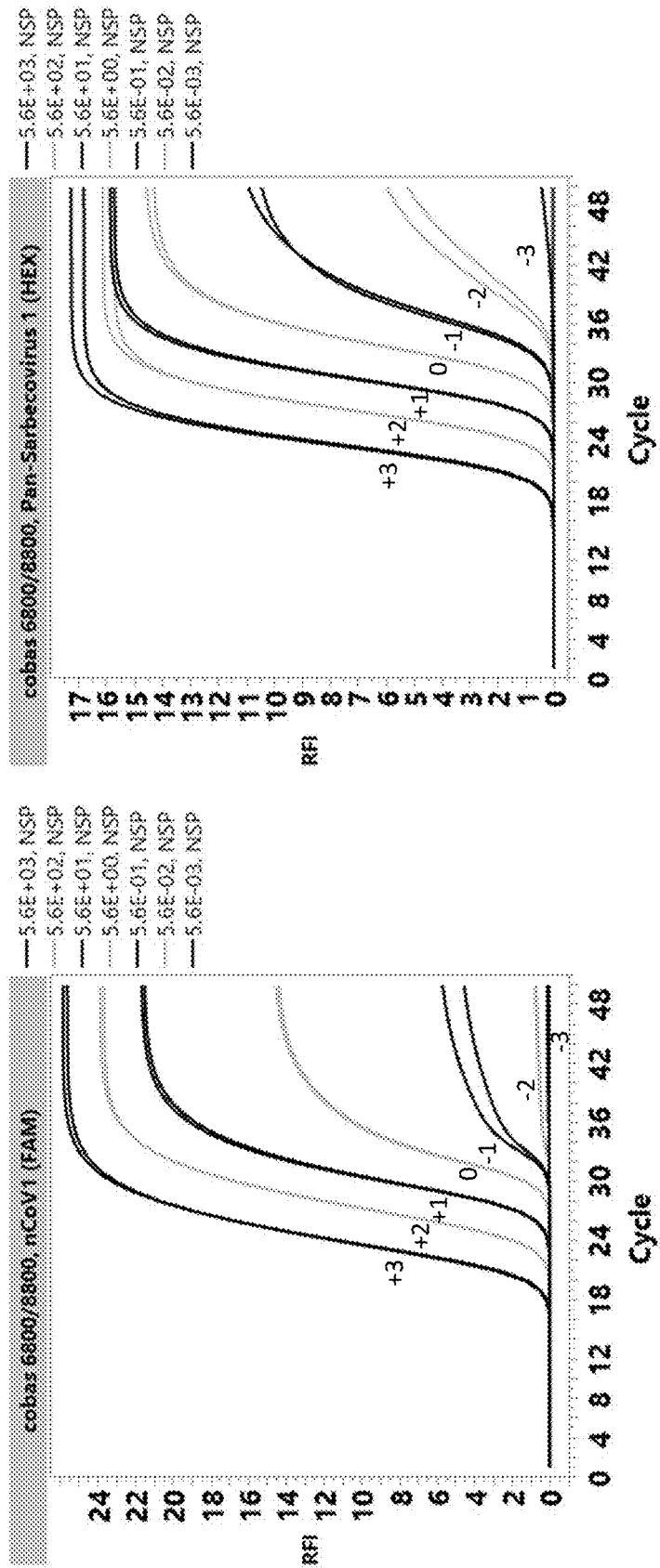
FIG. 8 shows the growth curves generated from the SARS-CoV-2 Test using isolated genomic RNA from a patient sample at the indicated levels diluted in Nasopharyngeal Sample Eluates (NSP) in a multiplex PCR test comprising the nCoV1 assay (left) and Pan-Sarbecovirus-1 assay (right).

A multiplex PCR test was performed on the genomic RNA isolated from the patient sample using the primer/probe set of the nCov1 assay (SEQ ID NOs: 1, 7, 21) and the Pan-Sarbecovirus-1 assay (SEQ ID NOs: 5, 15, 25) and the growth curves generated in SD and NSP matrices are shown in FIG. 7 and FIG. 8, respectively. The determined Ct values from this experiment are summarized in TABLE 8.

TABLE 8

Summary of Data from testing Genomic virus RNA in Contrived Samples

SARS-COV-2 Isolate USA-WA1/2020

| Serial Dilutions (TCID$_{50}$/mL Equivalents) | Cycle Threshold (Ct) nCoV1 target (FAM) | | Cycle Threshold (Ct) Pan-Sarbecovirus-1 target (HEX) | |
|---|---|---|---|---|
| | NSP (n = 2) | SD *(n = 3) **(n = 10) | NSP (n = 2) | SD *(n = 3) **(n = 10) |
| 2.80E+04 | 19.5 | 19.5* | 19.5 | 19.4* |
| 2.80E+03 | 22.8 | 22.9* | 23.0 | 22.7* |
| 2.80E+02 | 25.7 | 26.2** | 26.0 | 26.1** |
| 2.80E+01 | 28.6 | 29.4** | 28.9 | 29.3** |
| 2.80E+00 | 30.5 | 32.6** | 31.4 | 32.7** |
| 2.80E−01 | 31.6 | 35.2** | 33.8 | 35.7** |
| 2.80E−02 | # | 37.7** | 37.8 | 38.2** |

\# Amplification not observed
NSP = Nasopharyngeal Swab Specimen Eluate and
SD = Specimen Diluent The testing of SARS-CoV-2 Isolate USA-WA1/2020 genomic RNA in the specimen diluent shows that the SARS-CoV-2 test was able to detect down to $5.6E^{-03}$ TCID50 equivalent input (assuming 100% extraction efficiency). Comparing the genomic RNA data to synthetic transcript copy number data, this translates to an equivalent of ~10 copies of target template detection. Furthermore, these results demonstrated that the SARS-CoV-2 test could detect Isolate USA-WA1/2020 genomic RNA in nasopharyngeal matrix (Contrived NSP System).

Example 7: Exclusivity/Cross-Reactivity Studies of SARS-CoV-2 Test

The SARS-CoV-2 test was evaluated for the exclusivity/cross-reactivity against other respiratory viruses including MERS and four Coronaviruses (229E, OC43, HKU1 and NL63). The list of all the virus nucleic acid eluates evaluated are shown on TABLE 9. No interaction with SARS-CoV-2 were observed, demonstrating the specificity of this test.

TABLE 9

List of Organisms Tested in Exclusivity Studies

| Virus | Vendor | Cat. No. |
|---|---|---|
| CoV OCAS (Betacoronavirus 1) | ATCC | V8-1558 |
| CoV 2295 | ATCC | VR-740 |
| Cov OC43 | ZeptoMatrix | NATRVP-IDI |
| CoV 229E | ZeptoMetrix | NATRVP-IDI |
| COV NL63 | ZeptoMetrix | NATRVP-IDI |
| COV HKU1 | ZeptoMetrix | NATRVP-IDI |
| Microbiologies (21 targets) Respiratory Panel | Microbiologics | 8217 |
| CoV 229E | Development - Rotkreuz | Patient Sample |
| CoV NL63/Influenza B | Development - Rotkreuz | Patient Sample |
| CoV OC43 | Development - Rotkreuz | Patient Sample |
| CoV OC43 | Developnient - Rotkreuz | Patient Sample |
| CoV OC43 | Developnient - Rotkreuz | Patient Sample |
| CoV 229E | Development - Rotkreuz | Fstient Sample |
| CoV 229E | Development - Rotkreuz | Patient Sample |
| Enterovirus/CoV 229E | Development - Rotkreuz | Patient Sample |
| Enterovirus/CoV OC43 | Developnient - Rotkreuz | Patient Sample |
| CoV 229E | Development - Rotkreuz | Patient Sample |
| CoV NL63 | Development - Rotkreuz | Patient Sample |
| COV NL63 | Developnient - Rotkreuz | Patient Sample |
| Enterovirus/CoV OC43 | Development - Rotkreuz | Patient Sample |
| Cornavirus 229E/CoV OC43 | Development - Rotkreuz | Patient Sample |
| Cornavirus 229E/CoV OC43 | Developnient - Rotkreuz | Patient Sample |
| RPNEG | Exact Diagnostics | RPNEG |
| RPPOS | Exact Diagnostics | RPPOS |
| RPRC: MIX1 | Exact Diagnostics | RPRC |
| RPRC: MIX2 | Exact Diagnostics | RPRC |
| RPRC: MIX3 | Exact Diagnostics | RPRC |

TABLE 9-continued

List of Organisms Tested in Exclusivity Studies

| Virus | Vendor | Cat. No. |
|---|---|---|
| RPRC: MixA | Exact Diagnostics | RPRC |
| RSV A (2006 iso) | ZeptoMetrix | Internal Eluate |
| FluA H1N1 | Internal Elvate | Internal Eluate |
| FluA H3N2 A/Brisbane/10/07 | ZeptoMatrix | NATRVP-IDI |
| FluB Brisbane/60/08 | ZeptoMetrix | Internal Eluate |
| HMPV 8, Peru6-2003 | ZeptoMetrix | NATRVP-IDI |
| AdV4 (E) | ZeptoMetrix | 810070CF |
| AdV3 (B) | ZeptoMetrix | 810062CF |
| AdV5 (C) | ZeptoMetrix | 810020CF |
| Enterovirus 71, Strain H | ATCC | VR-1432 |
| Echoviras 30, Bastianni | ATCC | VR-1660 |
| Coxacievirus A24, DN-19 | ATCC | VR-1662 |
| EV D68, US/MO/14-18947 | ATCC | VR-1823 |
| Rhinovinas A | ZeptoMetrix | NATRVP-IDI |
| MPIV1 | ZeptoMetrix | NATRVP-IDI |
| HPIV2 | ZestoMetrix | NATRVP-IDI |
| HPIV3 | ZeptoMetrix | NATRVP-IDI |
| MPIV4 | ZeptoMetrix | NATRVP-IDI |
| Bordetella pertussis | ZeptoMetrix | NATRVA-IDI |
| Influenzs B, B/Florida/02/06 | ZeptoMetrix | NATRVP-IDI |
| Chlamydophila pneumoniae | ZeptoMatrix | NATRVP-IDI |
| CoV 229E RNA | ATCC | VR-740DQ |
| CoV NL63 RNA | ATCC | VR-32635D |
| CoV OC43 RNA | ATCC | VR-1558D |
| CoV HKU1 RNA | ATCC | VR-32625D |
| MERS RNA | ATCC | VR-32485D |

Example 8: SARS-CoV-2 and Influenza A/B Assay Description

The SARS-CoV-2 and Influenza A/B Test is a multiplex single well assay that detects the SARS-CoV-2, Influenza A and Influenza B viral RNA genome sequences using four different channels: the SARS-CoV-2 dual targets (i) specific nucleic acid sequences from the non-structural Open Reading Frame (ORF1a/b) in the genome of the SARS-CoV-2 in one channel and (ii) the conserved sequence structural Envelope (E) Gene location common to all Sarbecoviruses including SARS-CoV-2 in a second channel; a third channel detects the Influenza A Segment 7 matrix protein 2 (M2) and matrix protein 1 (M1) sequences, and the Influenza B Segment 8 nuclear export protein (NEP) and nonstructural protein 1 (NS1) sequences are detected in the fourth channel. Results are for the specific detection of SARS-CoV-2, Influenza A and Influenza B viral RNA genome sequences are detectable in nasopharyngeal and oropharyngeal swab samples during the acute phase of infection.

The SARS-CoV-2 & Influenza A/B test can be run on the Cobas® 6800/8800 Systems, which are fully automated systems FDA approved/cleared for use with a variety of diagnostic tests, for sample preparation (nucleic acid extraction and purification) followed by PCR amplification and detection. Selective amplification of target nucleic acid from the sample is achieved by the use of target-specific forward and reverse primers. The master mix contains detection probes which are specific for SARS-CoV-2, Influenza A, and Influenza B, and the RNA Internal Control nucleic acid. The SARS-CoV-2, Influenza A, Influenza B and RNA Internal Control detection probes are each labeled with unique fluorescent dyes that act as a reporter. Amplification of RNA Internal Control is achieved by the use of non-competitive sequence specific forward and reverse primers, which have no homology with SARS-CoV-2, Influenza A, and Influenza B genome. A thermostable DNA polymerase enzyme is used for amplification. Each probe also has a second dye that acts as a quencher. The workflow uses the commercial Cobas® generic reagents (MGP cassette, Lysis Buffer, Specimen Diluent, Wash Buffer) together with the already existing reagent cassette with existing proteinase, elution buffer, MMX R1 (cofactor) and an internal control are planned to be used together with aforementioned new developed reagents. Nucleic acid from patient samples and added RNA-Internal Control molecules (same as the existing RNA QS reagent) are simultaneously extracted. External controls (positive and negative) are processed in the same way with each SARS-CoV-2 & Influenza A/B run.

Example 9: SARS-CoV-2 and Influenza A/B Assay Design Strategy

The diagnostic test is designed for the detection and discrimination of the 2019 novel coronavirus (SARS-CoV-2), Influenza A, and Influenza B. For the SARS-CoV-2 assay, a dual target assay was designed for the detection of SARS-CoV-2 in the one channel (FAM) and Sarbecovirus subgenus family that also includes SARS-CoV-2 in another channel (HEX). Also, the assay was designed to detect the Influenza A sequences in the third channel (COU) and the Influenza B sequences in the fourth channel (JA270). The SARS-CoV-2 assays have 6 oligonucleotides: one Reverse Transcription (RT) primer each for the 2 genomic regions, one non-RT primer each, and one probe each labeled with a FAM and HEX fluorophore. The influenza A assay contains one RT primer, one non-RT primer, and a probe labeled with the COU fluorophore. It detects the influenza A segment 7 matrix protein 2 (M2) and matrix protein 1 (M1) RNA sequences. The influenza B assay is also designed as a Pan-Flu B assay to detect all common influenza B strains including the two influenza B lineages: B/Yamagata and B/Victoria. The assay contains one RT primer, one non-RT primer, and a probe labeled with the JA270 fluorophore. It detects the influenza B segment 8 nuclear export protein (NEP) and nonstructural protein 1 (NS1) sequences.

Example 10: SARS-CoV-2 and Influenza A/B Assay Primer and Probe Selection

Figure 9A:
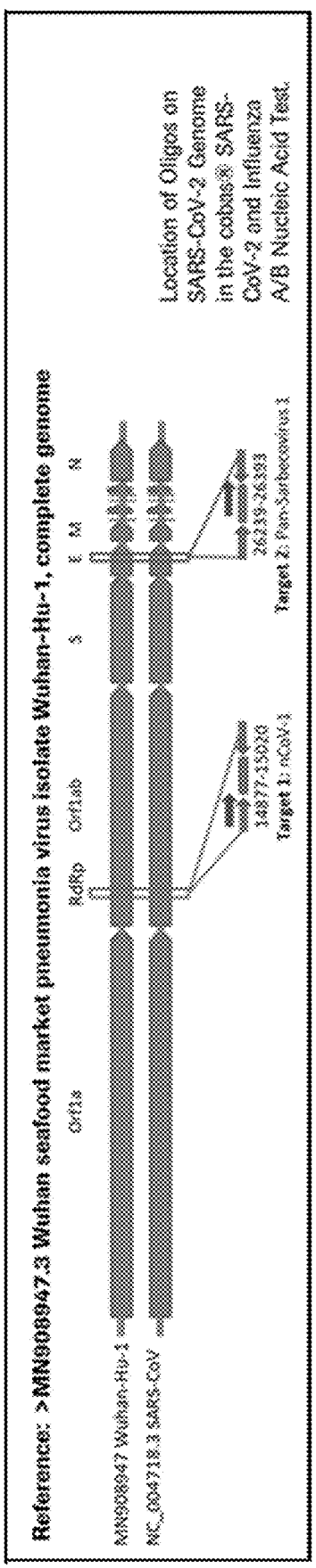
FIG. 9A shows the genome organization of SARS-CoV-2 (labeled here as Wuhan-Hu-1) and SARS-CoV and the locations of the target regions of the SARS-CoV-2 primer and probes for the SARS-CoV-2 & Influenza A/B assay.
Figure 9B:
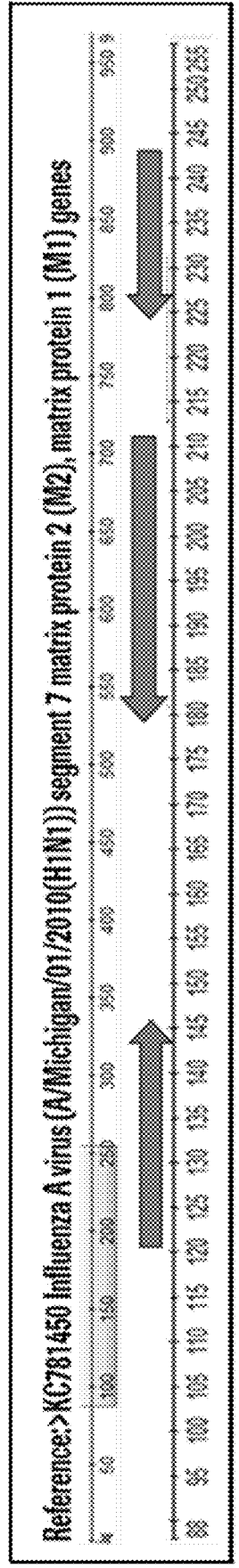
FIG. 9B shows the locations of the target regions of the influenza A primer and probes for the SARS-CoV-2 & Influenza A/B assay.
Figure 9C:
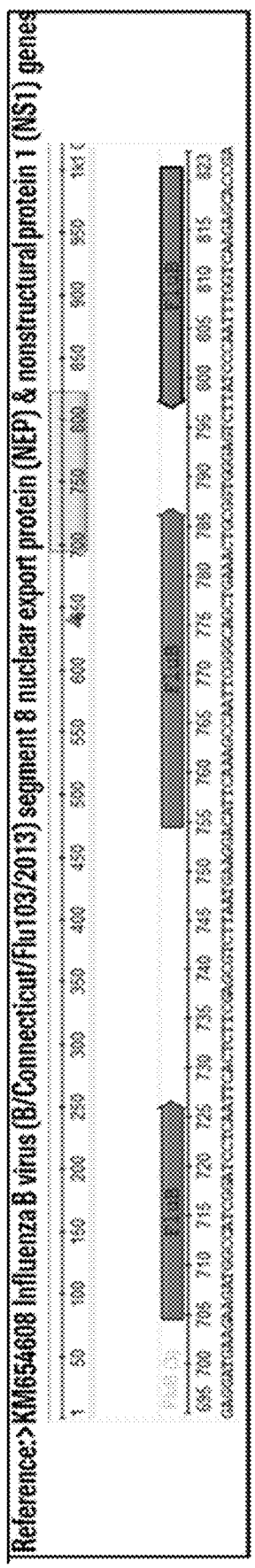
FIG. 9C shows the locations of the target regions of the influenza B primer and probes for the SARS-CoV-2 & Influenza A/B assay.

The master mix contains detection probes which are specific for the coronavirus type SARS-CoV-2, members of the Sarbecovirus subgenus, and detection probes for Influenza A and Influenza B, and the RNA Internal Control nucleic acid, respectively each with a unique fluorophore. The relative locations of the amplicon targets on the SARS-CoV-2, influenza A and influenza B genomes are shown on FIG. 9A, FIG. 9B, and FIG. 9C, respectively. Select combination set of primers and probes are shown in TABLE 10.

TABLE 10

Assay and Oligonucleotides Screened

| Assay Name | Target Gene | Oligo Name | SEQ ID NO: |
|---|---|---|---|
| FluA | Segment 7 M2/M1 | FLUAF M1 121 146 | 33 |
|  |  | FLUA_RP4_A | 34 |
|  |  | FLUAP.H.C3_M1_212_181.6COU1.C | 35 |
| nCoV1 | ORF1a/b | NCOV-1-FN1.A | 27 |
|  |  | NCOV-1R.A | 7 |
|  |  | WUHAN-4P.P | 21 |
| Pan-Sarbecovirus | Envelope | SARBV-1F2.A | 6 |
|  |  | SARBV-1R.A | 18 |
|  |  | SARBV_P1-N2_6Q.C3 | 32 |
| FluB | Segment 8 NEP/NS1 | FLUBF NS1.749 770 | 36 |
|  |  | FLUBR_S1.865_842 | 37 |
|  |  | FLUB_PRB2_11Q_JA270.C3 | 38 |

Example 10: Performance Assessment of SARS-CoV-2 & Influenza A/B Test

Feasibility assessment of components (including the select combination of primers and probes shown in TABLE 10), workflows and assay reagents for the combined SARS-CoV-2 & Influenza A/B test is based on experimental evaluation by research using the Cobas® 6800 reagents. Linearized recombinant plasmids were tested with the assay oligonucleotides to assess performance. In vitro transcripts were also generated to evaluate performance of the assays using synthetic RNA. Nucleic acid quantitation was done using Qubit with DNA and RNA standards. Plasmid DNA and transcripts were serially diluted in MultiPrep Specimen Diluent Buffer (MPSD, also known as BGSD) and used in assay performance studies. Internal control oligonucleotide (generic internal control, GIC) were included in the evaluations with both linearized DNA and RNA transcripts. Experiments were conducted on the Roche Z480 with 6800 filters Cycler that was fitted and calibrated with the Cobas® 6800 filters using the Cobas® 6800 generic Thermocycling profile which was described in Example 4.

Nasopharyngeal (NPS) samples were obtained from patients exhibiting upper respiratory symptoms using flocculated swabs and collected in Universal Viral Transport Medium (3 mL). These samples were characterized by in-house developed PCR assays and shown to exclude the following viruses: FluA, FluB, RSV, HMPV, AdV, EV/RV and HPIV1, HPIV2, HPIV3, HPIV4 and human Coronaviruses (229E, NL63, HKU1 and OC43) by MiSeq sequencing of PCR products. These NPS samples were stored frozen at −70° C., thawed and used in experiments as needed. A modified sample preparation workflow (Process and Elute, P&E) was used on the Cobas® 6800 System wherein either 300 or 400 μL of NPS sample was processed to prepare nucleic acid eluates. These eluates contain the gIC armored RNA (QS RNA Control) that follow the same NPS sample preparation process on the Cobas® 6800 system and serves as the internal sample processing control. Eluates were then used in studies with the SARS-CoV-2 assays with amplification and detection on the Z480 with 6800 Filters cycler and/or the Cobas® 6800 analytical cycler.

Figure 10:
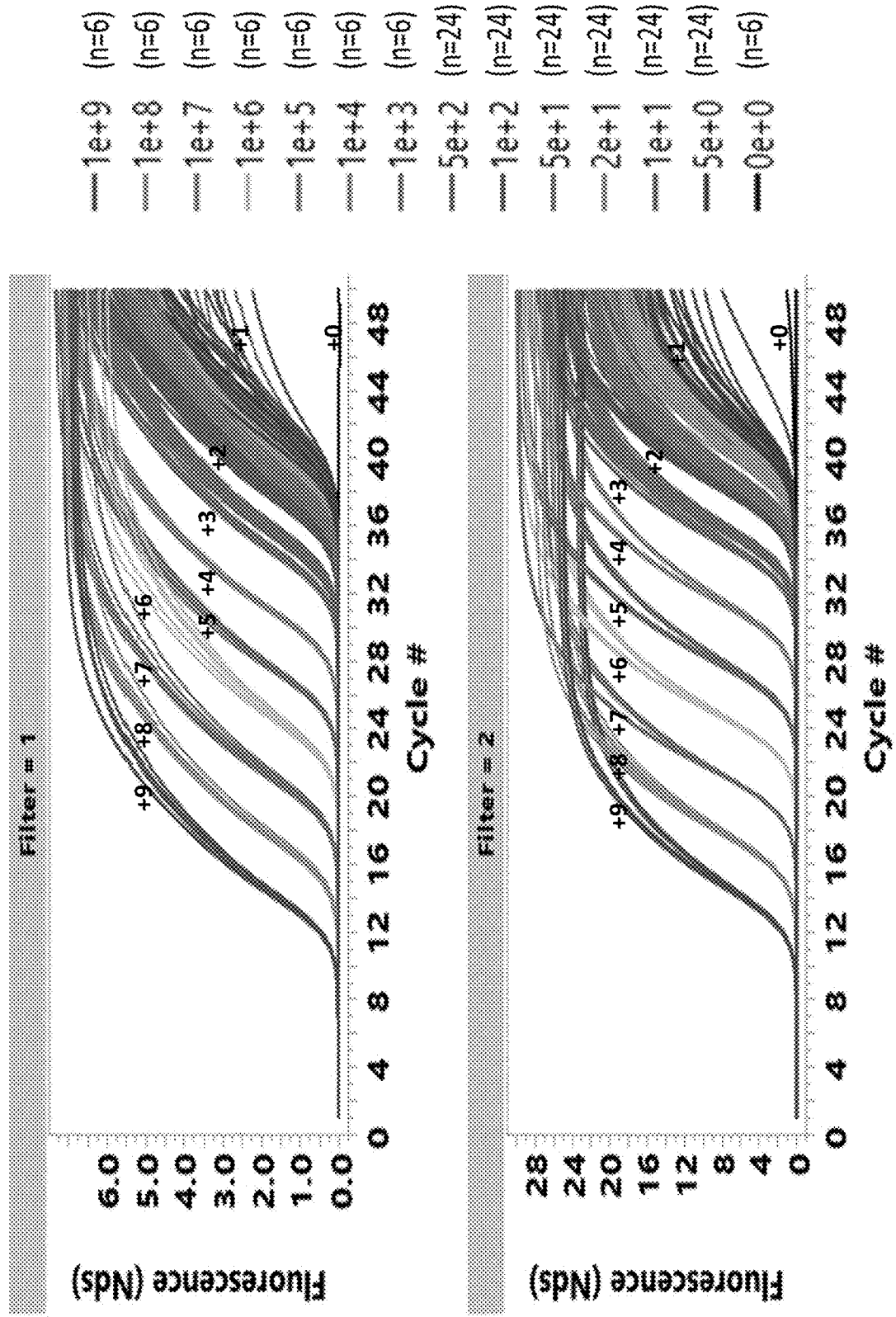
FIG. 10 shows the growth curves in the multiplex PCR test described in Example 11 for the FluA assay (top, Filter=1) and the nCoV1 assay (bottom, Filter=2), and across the indicated levels (1e+9 to 5e+0) tested using the synthetic in vitro transcripts.
Figure 11:
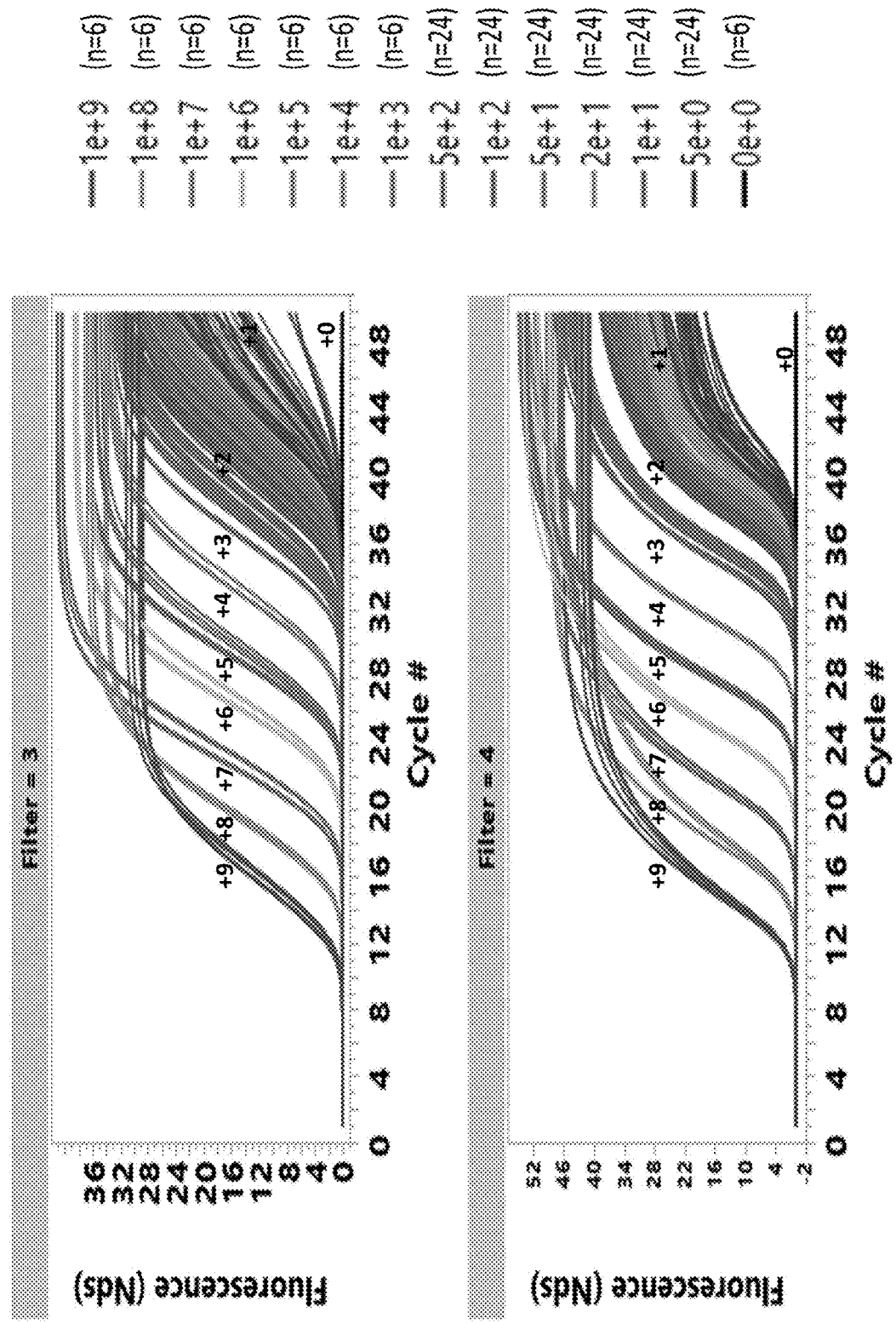
FIG. 11 shows the growth curves in the multiplex PCR test described in Example 11 for the Pan-Sarbecovirus-1 assay (top, Filter=3) and the FluB assay (bottom, Filter=4), and across the indicated levels (1e+9 to 5e+0) tested using the synthetic in vitro transcripts.
Figure 12:
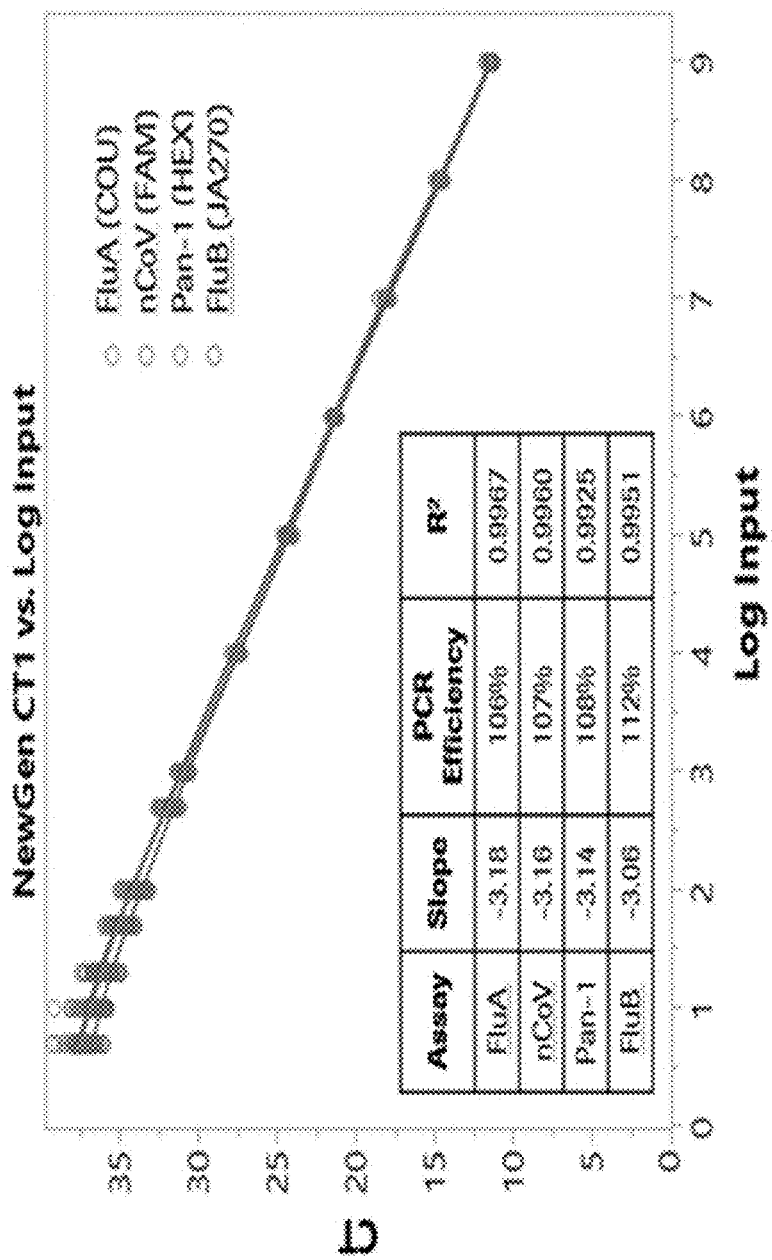
FIG. 12 shows the combined linearity plots (Ct charts with dynamic range plotted) for growth curves shown in FIG. 10 and FIG. 11.

Example 11: Linearity and Limit of Detection Using Transcripts in Clean System Using the combination set of primers and probes listed on TABLE 10, experiments were done initially with synthetic transcripts corresponding to each target assay region using a clean system (BGSD). Four transcripts were pooled at high copy levels and tested on the 6800 at several dilution levels (more replicates at lower levels). The results in FIG. 10, FIG. 11, FIG. 12, and TABLE 11 show good reproducibility at high input levels, low standard deviation at lower input levels and only one dropout each at the 5 cp/PCR for the Pan-Sarbecovirus and FluB assays. Excellent sensitivity of each assay with a broad dynamic range (1E+9 to 1E+1cp) in PCR was demonstrated. Good linearity and high PCR efficiencies ranging from 106% to 112% were observed for the SARS-CoV-2, Influenza A and Influenza B targets.

TABLE 11

Hit rate for each transcript and standard deviation for each assay

| | | Std Dev | | | |
|---|---|---|---|---|---|
| Input | # of Replicates | FluA (COU) | nCoV (FAM) | Pan-Sarbecovirus (HEX) | FluB (JA270) |
| 1E+09 | 6/6 | 0.09 | 0.05 | 0.28 | 0.08 |
| 1E+08 | 6/6 | 0.11 | 0.09 | 0.17 | 0.10 |
| 1E+07 | 6/6 | 0.15 | 0.11 | 0.28 | 0.14 |
| 1E+06 | 6/6 | 0.08 | 0.08 | 0.18 | 0.10 |
| 1E+05 | 6/6 | 0.13 | 0.10 | 0.24 | 0.13 |
| 1E+04 | 6/6 | 0.10 | 0.07 | 0.17 | 0.08 |
| 1E+03 | 6/6 | 0.15 | 0.15 | 0.33 | 0.15 |
| 5E+02 | 24/24 | 0.27 | 0.22 | 0.4 | 0.23 |
| 1E+02 | 24/24 | 0.31 | 0.26 | 0.49 | 0.28 |
| 5E+01 | 24/24 | 0.32 | 0.35 | 0.47 | 0.35 |
| 2E+01 | 24/24 | 0.27 | 0.44 | 0.54 | 0.47 |
| 1E+01 | 24/24 | 0.46 | 0.31 | 0.83 | 0.37 |
| 5E+00 | 23/24* | 0.43 | 0.54 | 0.63 | 0.53 |
| NTC (0) | 6/6 | — | — | — | — |

Figure 13:
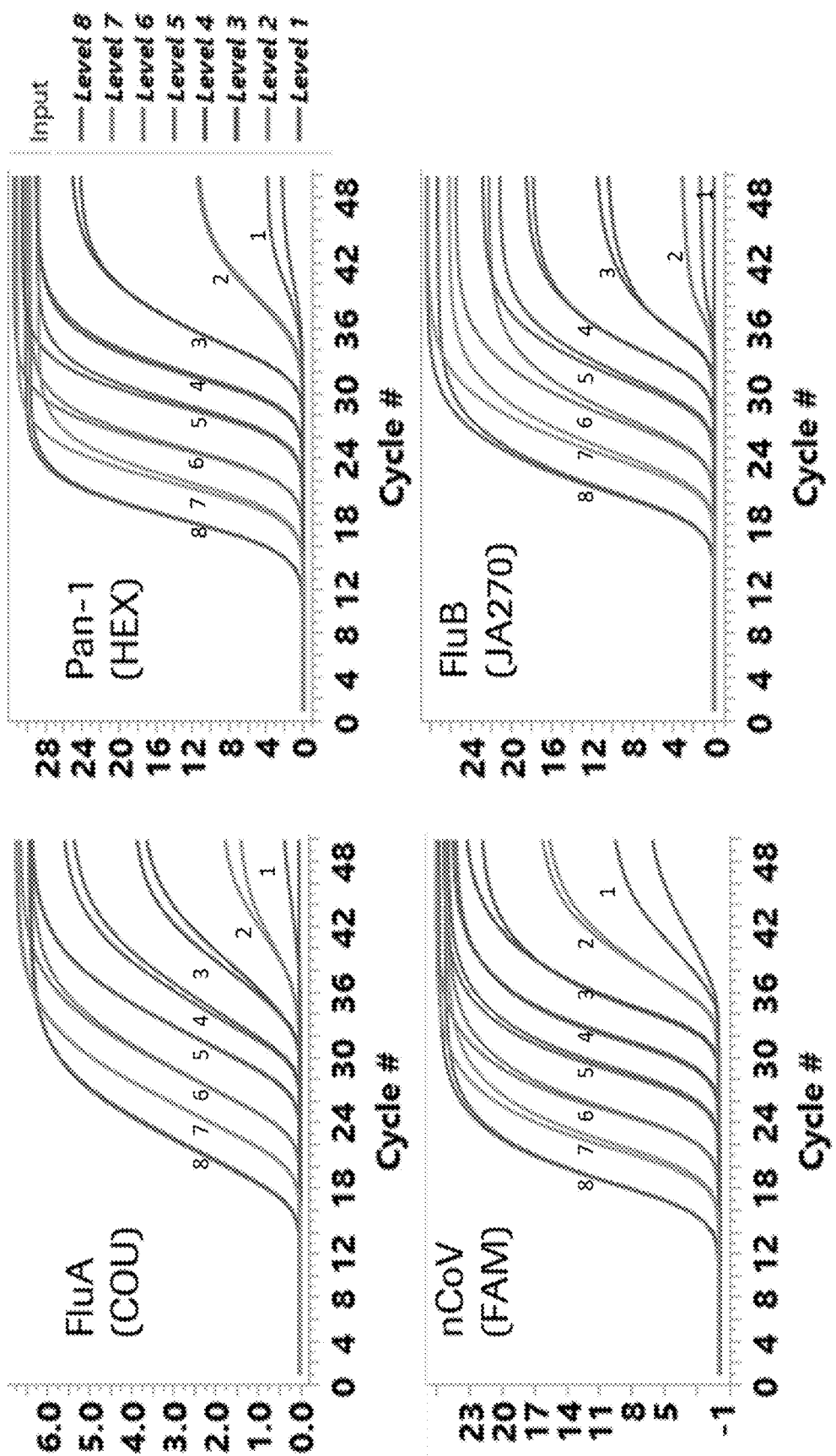
FIG. 13 shows the growth curves in the multiplex PCR test in contrived Nasopharyngeal Matrix as described in Example 12.

Example 12: Linearity Using Viral Cultures in Contrived Nasopharyngeal Matrix Three genomic RNA eluates from commercial viral cultures were pooled at high copy levels and tested on the Cobas® 6800 system at several dilution levels (n=2 per level). Results in TABLE 12 and FIG. 13 show good performance throughout the 8-log dynamic range, with all levels producing good, detectable signal. Using droplet digital PCR copy number estimates for each virus lot's TCID50, the low end detection per PCR calculates to <2 copies, <10 copies, and <30 copies for influenza A, SARS-CoV-2, and influenza B, respectively.

TABLE 12

| | Viral Eluate Input Amounts for Linearity Study | | |
|---|---|---|---|
| Level | Influenza A H1N1 Brisbane/59/07 Zeptometrix 0810244CF Lot 323919 | SARS-COV-2 USA-WA1/2020 Zeptometrix 0810587CFHI (Heat Inactivated) Lot 324443 Input Amount ($TCID_{50}$/mL) | Influenza B Florida/04/06 Zeptometrix 0810255CF Lot 312479 (sublot: 511120) |
| 8 | 6.7E+04 | 5.07E+05 | 1.9E+04 |
| 7 | 6.7E+03 | 5.07E+04 | 1.9E+03 |
| 6 | 6.7E+02 | 5.07E+03 | 1.9E+02 |
| 5 | 6.7E+01 | 5.07E+02 | 1.9E+01 |
| 4 | 6.7E+00 | 5.07E+01 | 1.9E+00 |
| 3 | 6.7E-01 | 5.07E+00 | 1.9E-01 |
| 2 | 6.7E-02 | 5.07E-01 | 1.9E-02 |
| 1 | 6.7E-03 | 5.07E-02 | 1.9E-03 |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for simultaneously detecting SARS-COV-2, influenza A, and influenza B in a sample comprising:

performing an amplifying step wherein the sample is contacted with a first set of primers, a second set of primers, and a third set of primers to produce one or more amplification products if SARS-COV-2, and/or influenza A, and/or influenza B is present in the sample, wherein the first set of primers produces an amplification product if SARS-COV-2 is present in the sample, the second set of primers produces an amplification product if influenza A is present in the sample, and the third set of primers produces an amplification product if influenza B is present in the sample;

performing a hybridizing step wherein the amplification product(s) are contacted with three or more detectable probes, wherein the three or more detectable probes include at least one probe specific for the amplification products of each of the first, the second, and the third sets of primers; and detecting the presence or absence of the amplified products, wherein the presence of the amplified product is indicative of the presence of SARS-COV-2, and/or influenza A, and/or influenza B in the sample and wherein the absence of the amplified product is indicative of the absence of SARS-COV-2, and/or influenza A, and/or influenza B in the sample, wherein:

the first set of primers comprises a forward primer comprising or consisting of an oligonucleotide sequence selected from the group consisting of SEQ ID NOS: 1-6, 27-31, and 40 or a complement thereof, and a reverse primer comprising or consisting of an oligonucleotide sequence selected from the group consisting of SEQ ID NOs: 7-20, and 41 or a complement thereof;

the first detectable probe comprises or consists of an oligonucleotide sequence selected from the group consisting of SEQ ID NOs: 21-26, 32 and 42-43 or a complement thereof;

the second set of primers comprises a forward primer comprising or consisting of an oligonucleotide sequence of SEQ ID NO: 33 or a complement thereof and a reverse primer comprising or consisting of an oligonucleotide sequence of SEQ ID NO: 34 or a complement thereof;

the second detectable probe comprises or consists of an oligonucleotide sequence selected from the group consisting of SEQ ID NOs: 35 and 44 or a complement thereof;

the third set of primers comprises a forward primer comprising or consisting of an oligonucleotide sequence of SEQ ID NO: 36 or a complement thereof and a reverse primer comprising or consisting of an oligonucleotide sequence of SEQ ID NO: 37 or a complement thereof; and the third detectable probe comprises or consists of an oligonucleotide sequence selected from the group consisting of SEQ ID NOs: 38 and 45 or a complement thereof.

2. The method of claim 1 wherein:

the first set of primers comprises a forward primer comprising or consisting of an oligonucleotide sequence of SEQ ID NO: 27 and a reverse primer comprising or consisting of an oligonucleotide sequence of SEQ ID NO: 7; and the first detectable probe for detecting the amplification product comprises or consists of an oligonucleotide sequence of SEQ ID NO: 21.

3. The method of claim 1 further comprising a fourth set of primers that produces an amplification product if SARS-COV-2 or SARS-COV-2 and other coronavirus target nucleic acids from the subgenus Sarbecovirus is present in the sample.

4. The method of claim 3 wherein:

the first set of primers comprises a forward primer comprising or consisting of an oligonucleotide sequence selected from the group consisting of SEQ ID NOs: 1-3 and 27-31 and a reverse primer comprising or consisting of an oligonucleotide sequence selected from the group consisting of SEQ ID NOs: 7-14;

the first detectable probe comprises or consists of an oligonucleotide sequence selected from the group consisting of SEQ ID NOs: 21-23, and 42;

the fourth set of primers comprises a forward primer comprising or consisting of an oligonucleotide sequence selected from the group consisting of SEQ ID NOs: 4-6, and 40, and a reverse primer comprising or consisting of an oligonucleotide sequence selected from the group consisting of SEQ ID NOs: 15-20, and 41; and the fourth detectable probe comprises or consists of an oligonucleotide sequence selected from the group consisting of SEQ ID NOs: 24-26, 32 and 43.

5. The method of claim 4 wherein:

the fourth set of primers comprises a forward primer comprising or consisting of an oligonucleotide sequence of SEQ ID NO: 5 and a reverse primer comprising or consisting of an oligonucleotide sequence of SEQ ID NO: 15; and the fourth detectable probe for detecting the amplification product comprises or consists of an oligonucleotide sequence of SEQ ID NO: 32.

6. The method of claim 4 wherein:

the fourth set of primers comprises a forward primer comprising or consisting of an oligonucleotide sequence of SEQ ID NO: 40 and a reverse primer comprising or consisting of an oligonucleotide sequence of SEQ ID NO: 41; and the fourth detectable probe for detecting the amplification product comprises or consists of an oligonucleotide sequence of SEQ ID NO: 43.

7. A kit for simultaneously detecting one or more nucleic acids of SARS-COV-2, one or more nucleic acids of influenza A, and one or more nucleic acids of influenza B in a sample comprising:

a) a first set of primers that produces a first amplification product if SARS-COV-2 is present in the sample, a second set of primers that produces a second amplification product if influenza A is present in the sample, and a third set of primers that produces a third amplification product if influenza B is present in the sample; and b) three or more detectable probes comprising a first detectable probe that specifically hybridizes to the first amplification product, a second detectable probe that specifically hybridizes to the second amplification product, and a third detectable probe that specifically hybridizes to the third amplification product, wherein:

the first set of primers comprises a forward primer comprising or consisting of an oligonucleotide sequence selected from the group consisting of SEQ ID NOs: 1-6, 27-31, and 40 or a complement thereof and a reverse primer comprising or consisting of an oligonucleotide sequence selected from the group consisting of SEQ ID NOs: 7-20, and 41 or a complement thereof;

the first detectable probe comprises or consists of an oligonucleotide sequence selected from the group consisting of SEQ ID NOs: 21-26, 32 and 42-43 or a complement thereof;

the second set of primers comprises a forward primer comprising or consisting of an oligonucleotide sequence of SEQ ID NO: 33 or a complement thereof and a reverse primer comprising or consisting of an oligonucleotide sequence of SEQ ID NO: 34 or a complement thereof;

the second detectable probe comprises or consists of an oligonucleotide sequence selected from the group consisting of SEQ ID NOs: 35 and 44 or a complement thereof;

the third set of primers comprises a forward primer comprising or consisting of an oligonucleotide sequence of SEQ ID NO: 36 or a complement thereof and a reverse primer comprising or consisting of an oligonucleotide sequence of SEQ ID NO: 37 or a complement thereof; and the third detectable probe comprises or consists of an oligonucleotide sequence selected from the group consisting of SEQ ID NOs: 38 and 45 or a complement thereof.

8. The kit of claim 7 further comprising a fourth set of primers that produces a fourth amplification product if SARS-COV-2 or SARS-COV-2 and other coronavirus target nucleic acids from the subgenus Sarbecovirus is present in the sample and a fourth detectable probe that specifically hybridizes to the fourth amplification product.

9. The kit claim 8 wherein;

the first set of primers comprises a forward primer comprising or consisting of an oligonucleotide sequence selected from the group consisting of SEQ ID NOs: 1-3 and 27-31 and a reverse primer comprising or consisting of an oligonucleotide sequence selected from the group consisting of SEQ ID NOs: 7-14;

the first detectable probe comprises or consists of an oligonucleotide sequence selected from the group consisting of SEQ ID NOs: 21-23, and 42;

the fourth set of primers comprises a forward primer comprising or consisting of an oligonucleotide sequence selected from the group consisting of SEQ ID NOs: 4-6, and 40 and a reverse primer comprising or consisting of an oligonucleotide sequence selected from the group consisting of SEQ ID NOs: 15-20, and 41; and the fourth detectable probe comprises or consists of an oligonucleotide sequence selected from the group consisting of SEQ ID NOs: 24-26, 32, and 43.

10. The kit of claim 9 wherein:
the fourth set of primers comprises a forward primer comprising or consisting of an oligonucleotide sequence of SEQ ID NO: 5 and a reverse primer comprising or consisting of an oligonucleotide sequence of SEQ ID NO: 15; and the fourth detectable probe for detecting the amplification product comprises or consists of an oligonucleotide sequence of SEQ ID NO: 32.

11. The kit of claim 8 wherein:
the fourth set of primers comprises a forward primer comprising or consisting of an oligonucleotide sequence of SEQ ID NO: 40 and a reverse primer comprising or consisting of an oligonucleotide sequence of SEQ ID NO: 41; and the fourth detectable probe for detecting the amplification product comprises or consists of an oligonucleotide sequence of SEQ ID NO: 43.

12. The kit of claim 7 wherein:
the first set of primers comprises a forward primer comprising or consisting of an oligonucleotide sequence of SEQ ID NO: 27 and a reverse primer comprising or consisting of an oligonucleotide sequence of SEQ ID NO: 7; and the first detectable probe for detecting the amplification product comprises or consists of an oligonucleotide sequence selected from the group consisting of SEQ ID NO: 21 and 42.

* * * * *